United States Patent [19]

Galpin, deceased et al.

[11] Patent Number: 5,079,341

[45] Date of Patent: Jan. 7, 1992

[54] CYCLOSPORINS

[76] Inventors: Ian J. Galpin, deceased, late of Wirral; by Christine M. Galpin, heir, Ivy Cottage, Thornton Common Road, Thornton Hough, Wirral L63 4JU, both of England

[21] Appl. No.: 222,211

[22] Filed: Jul. 21, 1988

[30] Foreign Application Priority Data

Jul. 22, 1987 [GB] United Kingdom ................ 8717300

[51] Int. Cl.$^5$ ............................................... C07K 7/64
[52] U.S. Cl. ..................................... 530/321; 530/317
[58] Field of Search ..................... 530/317, 321; 514/9, 514/11, 885, 886, 914

[56] References Cited

U.S. PATENT DOCUMENTS

| | | | |
|---|---|---|---|
| 4,108,985 | 8/1978 | Ruegger et al. | 424/177 |
| 4,117,118 | 9/1978 | Harri et al. | 424/177 |
| 4,649,047 | 3/1987 | Kaswan | 514/11 |

FOREIGN PATENT DOCUMENTS

| | | |
|---|---|---|
| 0034567 | 8/1981 | European Pat. Off. |
| 2455859 | 6/1975 | Fed. Rep. of Germany |
| 2819094 | 11/1978 | Fed. Rep. of Germany |
| 2907460 | 9/1979 | Fed. Rep. of Germany |
| 2941080 | 5/1980 | Fed. Rep. of Germany |
| 1491509 | 11/1977 | United Kingdom |
| 2015339 | 9/1979 | United Kingdom |
| 1567202 | 5/1980 | United Kingdom |
| 2033398 | 5/1980 | United Kingdom |

OTHER PUBLICATIONS

Rudinger, Peptide Hormones, Parsons (Ed.), U. Park Press, pp. 1–7, (1976).
Talmadge et al., 13th International Congress of Chemotherapy, Virenna, Herberman et al. (ed.), pp. 203/19–35 (1983).
Wenger R. M., "Total Synthesis of 'Cyclosporin A' . . . ", *Helvetica Chimica Acta* 67 (Fasc. 2-Nr. 60): 502–525, 1984.
Traber, R. et al., "New Cyclopeptides from . . . ", *Helvetica Chimica Acta,* 60 (Fasc. 5-Nr. 158): 1568–1578, 1977.
Traber, R. et al., "Isolation and Structure Determination . . . ", *Helvetica Chimica Acta* 65 (Fasc. 5-Nr. 162): 1655–1677, 1982.
Rich, D. G. et al., "Synthesis and Antimitogenic Activities . . . ", *Journal of Medicinal Chemistry* 29(6): 978–984, 1986.
Wegner R., "Synthesis of Cyclosporine . . . ", *Transplantation Proceedings* 15(4): 2230–2241, 1983.
Hiestand, P. C. et al., "Comparison of the Pharmacological . . . ", *Immunology,* 55:249–255, 1985.
Ruegger, A. et al., "Cyclosporin A, a Peptide . . . ", *Helvetica Chimica Acta* 59 (Fasc. 4-Nr. 112): 1075–1092, 1976.
Traber, R. et al., "The Structure of Cyclosporin C", *Helvetica Chimica Acta* 60 (Fasc. 4-Nr. 122): 1247–1255, 1977.
Wenger R., "Chemistry of Cyclosporin", White, D. J. G. (ed.), *Cyclosporin A,* . . . (held in Cambridge, Sep. 1981) Chptr. 3:19–34, 1982.
Wenger, R. M., "Synthesis of Cyclosporine . . . ", *Angewandte Chemie* 24(2): 77–138, 1985.
Tung, R. D. et al., "BOP-Cl Mediated Synthesis . . . ", *Journal of Organic Chemistry* 51:3350–3354, 1986.
McDermott, J. R. et al., "N-Methylamino Acids in Peptide Synthesis . . . ", *Canadian Journal of Chemistry* 51:2555–2570, 1973.
Walgate, R., "Politics of Premature French Claim of Cure", *Nature* 318:3, 1985.
Stiller, C. R. et al., "Effects of Cyclosporine . . . ", *Science* 223:1362–1367, 1984.
Bueding; E. et al., "Antischistosomel Effects of Cyclosporin A", *Agents and Actions* 11(4):380–383, 1981.
Knight, S. C. et al., "Effect of Cyclosporine . . . ", *Transplantation Proceedings* 19(1):320, 1987.
Galpin, I. J. et al., "Synthesis of Cyclosporine Analogues", *Tetrahedron Letters* 28:6517–6520, 1987.
Galpin, I. J. et al., "Synthetic Studies of Cyclosporin Analogues", *Tetrahedron* 44(6):1783–1784, 1988.
Galpin, I. J. et al., "Solution Synthesis of N-Methylated . . . ", *Tetrahedron* 44(6):1685–1690, 1988.
Galpin, I. J. et al., "Synthesis of Linear Undecapeptide . . . ", *Tetrahedron* 44(6):1773–1782, 1988.
Galpin, I. J., "Synthesis of Two Linear Fragments . . . ", *Tetrahedron* 44(6):1763–1772, 1988.

(Abstract continued on next page.)

*Primary Examiner*—John Doll
*Assistant Examiner*—Christina Chan
*Attorney, Agent, or Firm*—Lieberman Rudolph & Nowak

[57] ABSTRACT

Cyclosporins having anti-bacterial activity useful as immuno suppressive and anti-inflammatory agents are provided, such as undecapeptides of the formula (I)

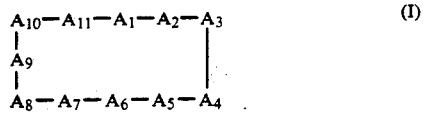

(I)

in which $A_1$ is either derived from 2-carboxyazetidine, 2-carboxypyrrolidine or 2-carboxypiperidine, or is an amino acid residue

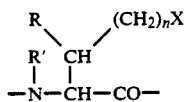

wherein n is 0, 1 or 2, X represents an amino, methylamino, mercapto or hydroxy group, R represents hydrogen or an acyclic aliphatic hydrocarbon group and R' represents hydrogen or methyl; $A_2$ is an amino acid residue

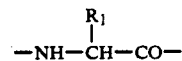

wherein $R_1$ is an acyclic aliphatic hydrogen group optionally substituted at the $C_1$ position of the group $R_1$ by an amino, methylamino, mercapto or hydroxy group, but with the proviso that when $R_1$ is a group of less than four carbon atoms then $A_1$ is a heterocyclic amino acid residue or is an amino acid residue $—R'—N—CH(CHR(CH_2)_nX)—CO—$ wherein either (a) R is hydrogen or (b) R is an acyclic aliphatic hydrocarbon group and either n is O and X is an amino, methylamino or mercapto group, or n is 1 or 2 and X is an amino, methylamino, mercapto or hydroxy group; $A_3$ is a sarcosine residue; $A_4$ is an N-methyl-leucine residue; $A_5$ is a valine residue; $A_6$ l is an M-methyl-leucine residue; $A_7$ is an alanine residue; $A_8$ is an alanine residue; $A_9$ is an N-methyl-leucine residue; $A_{10}$ is an N-methyl-leucine or sarcosine residue; and $A_{11}$ is an N-methylvaline residue.

1 Claim, 3 Drawing Sheets

CYCLOSPORINS

BACKGROUND OF THE INVENTION

The present invention relates to cyclosporin derivatives, their production and their use for therapy.

The cyclosporins comprise a group of cyclic, poly-N-methylated undecapeptides having valuable therapeutic properties, particularly as immunosuppressive and anti-inflammatory agents although it has been suggested that they may also be useful in the treatment of schistosomiasis (Bueding et al. Agents and Actions II, 1981, 380), diabetes (Stiller et al. Science, 1984, 223, 1362) and AIDS (Walgate, Nature, 1985, 318, 3).

SUMMARY OF THE INVENTION

It is an object of the present invention to provide cyclosporin analogues of modified structure.

Accordingly the present invention comprises a cyclosporin in which the amino acid residue at position 1 is either derived from 2-carboxyazetidine, 2-carboxypyrrolidine (proline) or 2-carboxypiperidine, which may optionally be substituted on a ring carbon atom other than that at position 2 by an amino, methylamino, mercapto or hydroxy group, said group optionally being in derivative form, and/or by an acyclic aliphatic hydrocarbon group, or is an amino acid residue

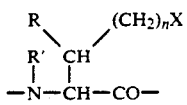

wherein n is 0, 1 or 2, X represents an amino, methylamino, mercapto or hydroxy group which may optionally be in derivative form, R represents hydrogen or, when n is 1 or 2 and X represents an amino, methylamino, mercapto or hydroxy group, or when n is 0 and X represents an amino, methylamino or mercapto group, R represents an acyclic aliphatic hydrocarbon group, and R' represents hydrogen or methyl; and/or the amino acid residue at position 2 is an amino acid residue

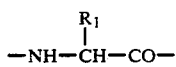

wherein $R_1$ represents an acyclic aliphatic hydrocarbon group of four or more carbon atoms optionally substituted at the $C_1$ position by an amino, methylamino, mercapto or hydroxy group or such a group in derivative form.

Examples of cyclosporins according to the present invention are known cyclosporins incorporating the residues just described at position 1 and/or position 2.

BRIEF DESCRIPTION OF THE DRAWINGS

FIG. 1a: Graph of $^3$H-Thymidine Uptake in counts per minute $\times 10^{-2}$ vs. Dose for

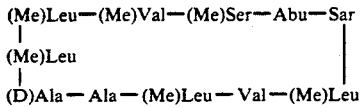

($A_1$) and cyclosporin A (CsA).

Figure 1A:
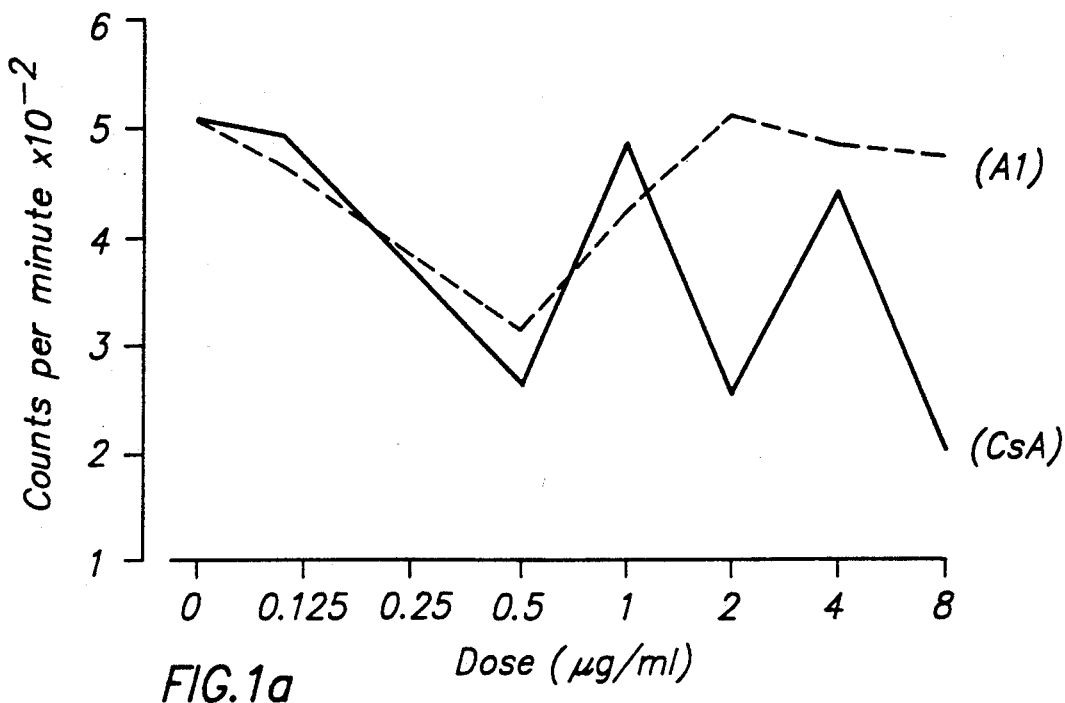
Figure 1B:
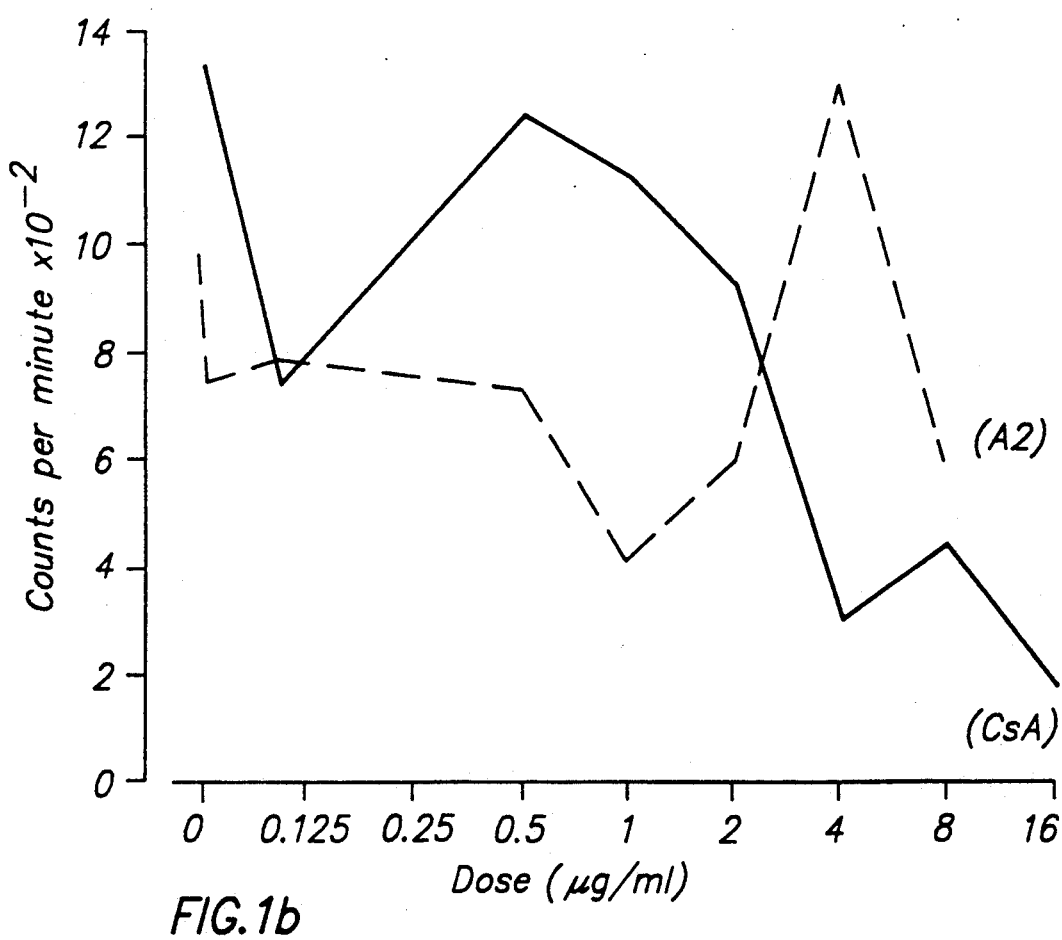

FIG. 1b: Graph of $^3$H-Thymidine Uptake in counts per minute $\times 10^{-2}$ vs. Dose for a stereoisomer of $A_1$ ($A_2$) and CsA.

Figure 1C:
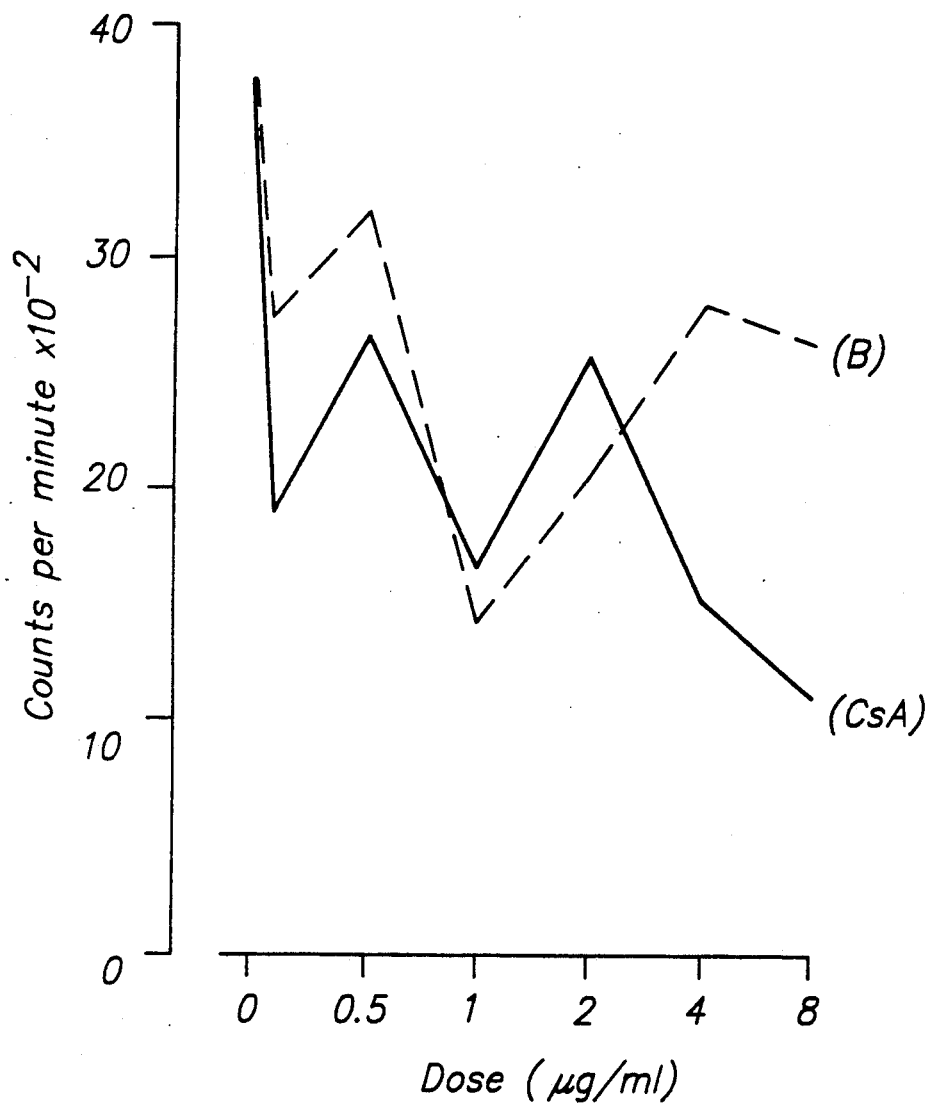

FIG. 1c: Graph of $^3$H-Thymidine Uptake in counts per minute $\times 10^{-2}$ vs. Dose for

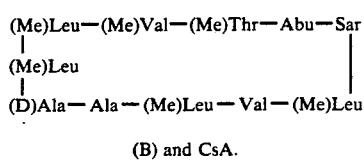

(B) and CsA.

Figure 1D:
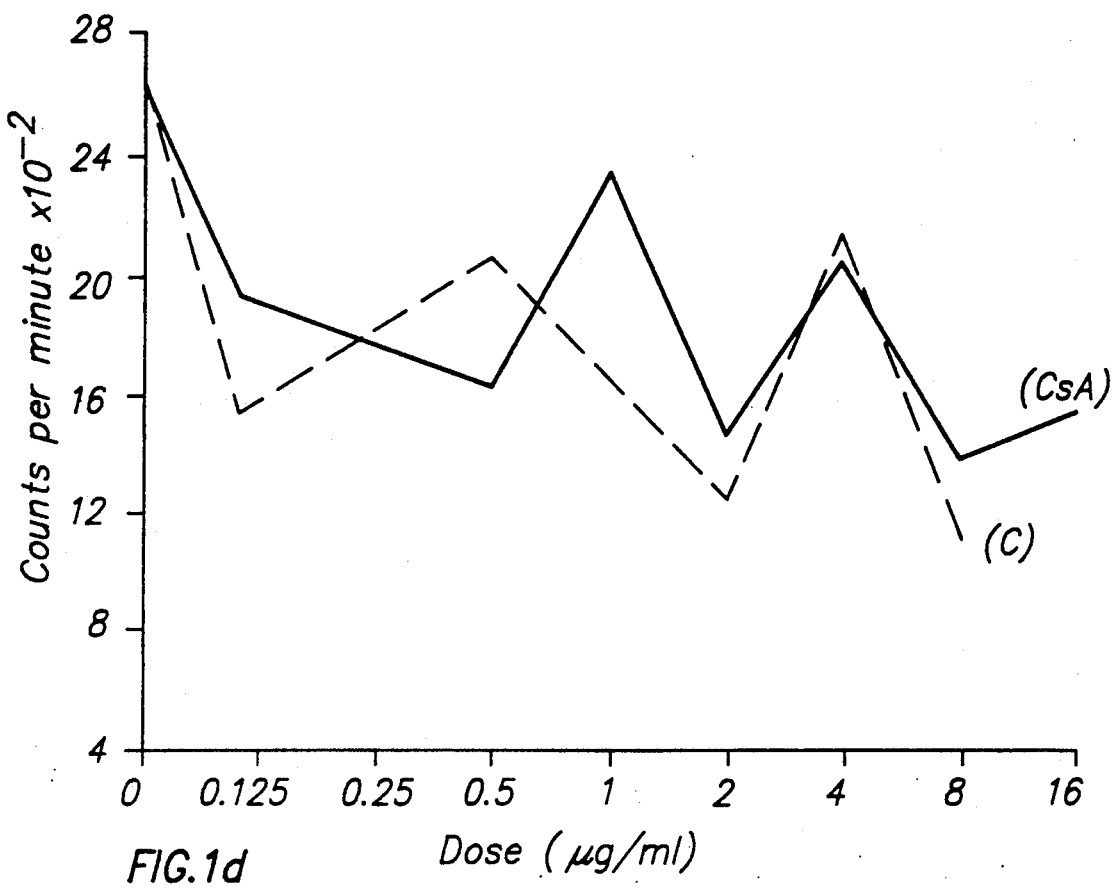

FIG. 1d: Graph of $^3$H-Thymidine Uptake in counts per minute $\times 10^{-2}$ vs. Dose for

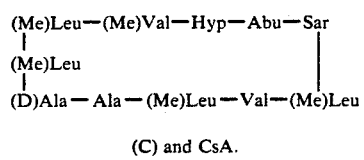

(C) and CsA.

Figure 1E:
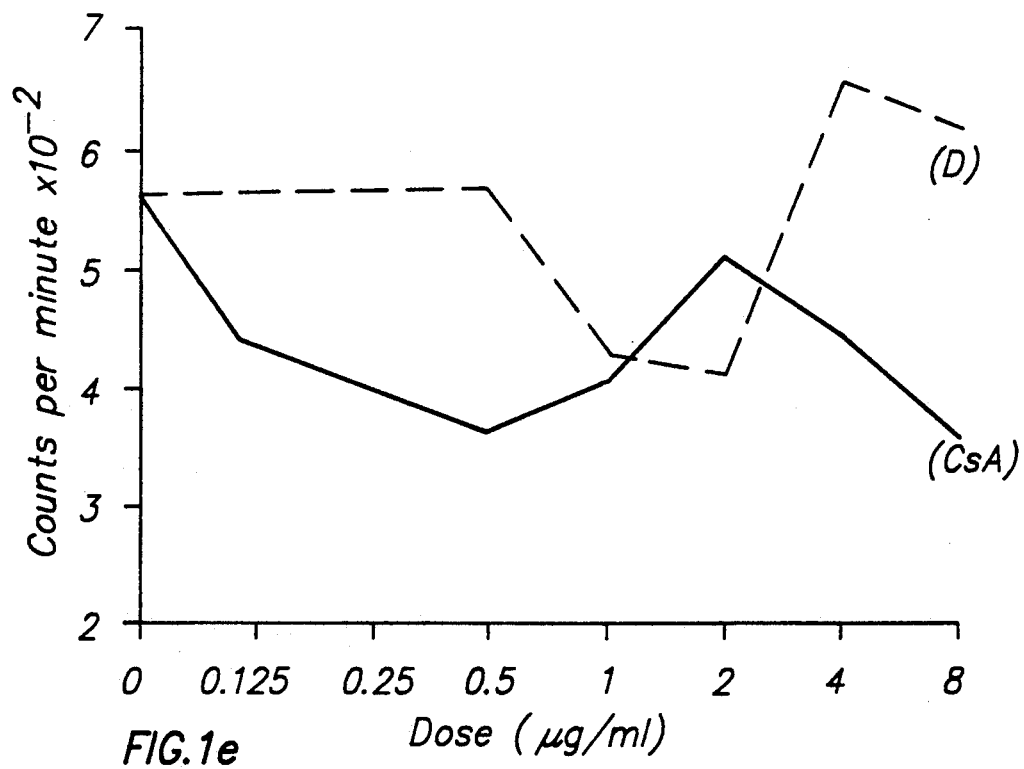

FIG. 1e: Graph of $^3$H-Thymidine Uptake in counts per minute $\times 10^{-2}$ vs. Dose for

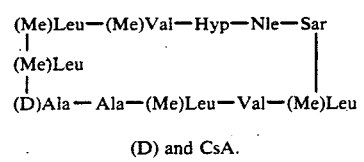

(D) and CsA.

DETAILED DESCRIPTION OF THE INVENTION

A preferred group of cyclic undecapeptides according to the present invention has the formula (I)

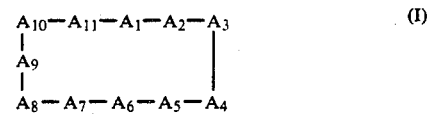

in which $A_1$ is either derived from 2-carboxyazetidine, 2-carboxypyrrolidine (proline) or 2-carboxypiperidine, which may optionally be substituted on a ring carbon atom other than that at position 2 by an amino, mercapto or hydroxy group and/or by an acyclic aliphatic hydrocarbon group, or is an amino acid residue

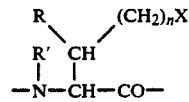

wherein n is 0, 1 or 2, X represents an amino, methylamino, mercapto or hydroxy group, R represents hydrogen or an acyclic aliphatic hydrocarbon group, for example of 1 to 10 and particularly of 1 to 6 carbon atoms, and R' represents hydrogen or methyl; $A_2$ is an amino acid residue

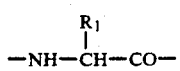

wherein $R_1$ is an acyclic aliphatic hydrocarbon group, for example of 1 to 6 carbon atoms, optionally substituted at the $C_1$ position of the group $R_1$ by an amino, methylamino, mercapto or hydroxy group, but with the proviso that when $R_1$ is a group of less than four carbon atoms then $A_1$ is a heterocyclic amino acid residue or is an amino acid residue —R'N—CH(CHR(CH$_2$)$_n$X-)—CO— wherein either (a) R is hydrogen or (b) R is an acyclic aliphatic hydrocarbon group and either n is 0 and X is an amino, methylamino or mercapto group, or n is 1 or 2 and X is an amino, methylamino, mercapto or hydroxy group; $A_3$ is a sarcosine residue; $A_4$ is an N-methyl-leucine residue; $A_5$ is a valine residue; $A_6$ is an N-methyl-leucine residue; $A_7$ is an alanine residue; $A_8$ is an alanine residue; $A_9$ is an N-methyl-leucine residue; $A_{10}$ is an N-methyl-leucine or sarcosine residue; and $A_{11}$ is an N-methylvaline residue; or such a cyclic undecapeptide in which one or more of any amino, methylamino, mercapto or hydroxy group present in $A_1$ or $A_2$ is in derivative form.

Preferences among the various residues constituting the undecapeptide (I) are as follows. Subject to the provisos expressed hereinbefore, the residue $A_1$ may conveniently contain a group (CH$_2$)$_n$X wherein n is 0 or particularly 1 and X is an amino (especially when n is 1) or a hydroxy group (especially when n is 0) and may conveniently contain a group R which is hydrogen or a $C_{1-6}$ alkyl or alkenyl group, for example an isopropyl, ethyl or particularly a methyl group, or especially a 1-methylpentyl or preferably a 1-methylpent-3-enyl group. In general, and particularly in the case of these last two mentioned groups R, R' is preferably methyl but it may conveniently also be hydrogen in some other cases, in particular in the case where R is hydrogen, n is 1 and X is amino. Groups $A_1$ of the type R'N—CH—(CHR(CH$_2$)$_n$X)—CO— of some particular interest thus have a group R' which is methyl or hydrogen, a group (CH$_2$)$_n$X which is hydroxy, or aminomethyl, and a group R which is hydrogen (especially when (CH$_2$)$_n$X is amino or aminomethyl and R' is hydrogen).

As regards the heterocyclic amino acid residues $A_1$, which are of some particular interest, those residues containing a 6-membered or particularly a 5-membered ring system are of most interest and these may conveniently be substituted by an amino, methylamino, mercapto or hydroxy group, particularly the last mentioned of these. Such substitution is of particular interest at the ring carbon atoms alpha and beta to that carrying the carboxy group. The ring may be substituted by an acyclic aliphatic hydrocarbon group (for example as described for R), more often in conjunction with substitution by an amino, methylamino, mercapto or hydroxy group and such substitution is again of most interest on the ring carbon atoms beta or particularly alpha to that carrying the carboxy group, and may conveniently be on the same carbon atom as that carrying an amino, methylamino, mercapto or hydroxy group. Preferred residues $A_1$ of this type are 3- and 4-hydroxy-2-carboxypiperidyl and especially 3- and 4-hydroxyprolyl (in either the cis or the trans configuration).

Subject to the provisos expressed hereinbefore, the residue $A_2$ may conveniently contain a group $R_1$ which is a $C_{1-6}$ alkenyl or particularly a $C_{1-6}$ alkyl group. Examples of such groups are isobutyl, isopropyl and methyl, and particularly n-butyl, n-propyl and ethyl. $R_1$ may also conveniently be a $C_{1-6}$ alkenyl or particularly a $C_{1-6}$ alkyl group substituted at the $C_1$ position thereof, particularly by a hydroxy group. Examples of such groups are any of those alkyl groups just specifically described for unsubstituted groups $R_1$ substituted but carrying a $C_1$ hydroxy group substituent, for instance 1-hydroxylpropyl and 1-hydroxy-1-methylethyl and especially hydroxymethyl and particularly 1-hydroxyethyl. $A_{10}$ may conveniently be an N-methyl-leucine residue.

As regards the stereochemistry of the compounds, certain configurations of the various residues are preferred. Thus, residues $A_1$ to $A_7$ and $A_9$ to $A_{11}$ are conveniently of the L-configuration at the alpha carbon atom, whilst residue $A_8$ is conveniently of the D-configuration. In residue $A_1$ the asymmetric carbon atom of the group CHR(CH$_2$)$_n$X may be of either configuration but is preferably of the L-configuration and in one of the preferred cases where R is a 1-methylpentyl or 1-methylpent-3-enyl group as shown below (X' being —CH$_2$—CH$_2$— or —CH=CH—) the relative configurations of $A_1$ at (a), (b) and (c) are preferably S,R,R although other stereochemistries (S,R,S and S,S,R) in which position (a) is S(L) may be considered as may the R,S,S configuration. When X' is —CH=CH— the arrangement of the double bond is conveniently trans.

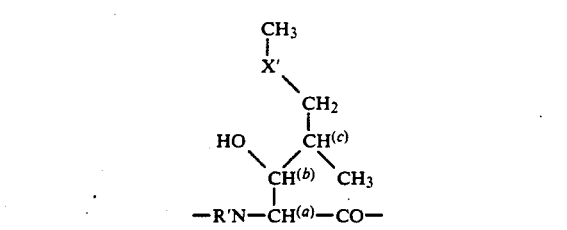

It will be appreciated that when the residue $A_1$ contains a substituted heterocyclic ring system the amino, methylamino, mercapto or hydroxy group may be cis or particularly trans to the residue of the carboxy group at the 2-position of the ring and where the ring is also substituted by an aliphatic hydrocarbon group further possibilities for isomerism will exist.

Examples of specific compounds according to the present invention include the compound (II) and derivatives thereof (all residues being of the L-configuration at the alpha carbon atom except where otherwise indicated and the full configuration of (Me)Bmt being S,R,R)

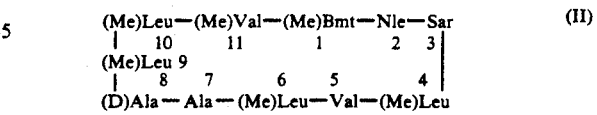

as well as variations of (II) in which (Me)Bmt is replaced by the dihydro version thereof [(4R)-4-but-1-yl-4-methyl-threonine], by (Me)Ser, (Me)Thr, (Me)Cys, Dab, Dpr or Hyp (or its 3-hydroxy equivalent) and/or in which Nle is replaced by Abu, Thr, Ser, Ala or Val but not when (Me)Bmt or (Me)Thr is present at position 1) and derivatives thereof. The abbreviations used in identifying the amino acids from which the residues are derived in (II) and variations thereof are as follows (Me in brackets indicating the N-methyl derivative of the amino acid):

| | |
|---|---|
| Bmt: (4R)-4-but-2E-en-1-yl-4-methyl-threonine | Thr: threonine |
| | Cys: cysteine |
| Abu: 2-aminobutyric acid | Dab: 2,4-diaminobutyric acid |
| Sar: sarcosine | Dpr: 2,3-diaminopropionic acid |
| Val: valine | Hyp: 4-hydroxyproline |
| Leu: leucine | Nva: norvaline |
| Ala: alanine | Nle: norleucine |
| Ser: serine | |

Cyclosporins according to the present invention are conveniently obtained by synthesis, for example through the cyclisation of an undecapeptide prepared by one of the various general methods of peptide synthesis which are described in the literature of peptide chemistry. Such methods generally involve the building up of a peptide from either the N- or more usually the C-terminus thereof either with single amino acids or with peptides containing a group of amino acids, the terminus of the added amino acid or peptide which it is desired should not react being protected by a group which is removed prior to the subsequent addition of the next amino acid or peptide and at least one of the reacting termini often being in activated form. It may also be necessary to protect certain additional reactive groups in some amino acids or peptides to prevent reaction occurring at these groups during the synthesis.

A preferred approach involves a synthesis, of either the solid phase or preferably the classical type, which builds up the linear undecapeptide H-$A_1$-$A_2$-$A_3$-$A_4$-$A_5$-$A_6$-$A_7$-$A_8$-$A_9$-$A_{10}$-$A_{11}$-OH starting from H-$A_{11}$-OH and successively adding peptides or preferably single amino acids thereto. By this means an octapeptide H-$A_4$-$A_5$-$A_6$-$A_7$-$A_8$-$A_9$-$A_{10}$$A_{11}$-OH and then a nonapeptide H-$A_3$-$A_4$-$A_5$-$A_6$-$A_7$-$A_8$-$A_9$-$A_{10}$-$A_{11}$-OH are obtained, in which $A_3$ to $A_{11}$ are as defined above with $A_{10}$ being a sarcosine or particularly an N-methyl-leucine residue, and the nonapeptide may then be used as an intermediate for the preparation of a range of undecapeptides H-$A_2$-$A_3$-$A_4$-$A_5$-$A_6$-$A_7$-$A_8$-$A_9$-$A_{10}$-$A_{11}$-OH containing a variety of residues $A_2$ and then of a range of undecapeptides containing a variety of residues $A_1$ and $A_2$, the nonapeptide being reacted successively with the two remaining amino acids to give the undecapeptide via the decapeptide or with a dipeptide H-$A_1$-$A_2$-OH to give the undecapeptide directly. These octapeptides, nonapeptides, decapeptides and undecapeptides, are therefore included by the present invention for their value as intermediates in the preparation of the cyclosporins. Such peptides may be in derivative form, such derivativisation involving one or more of the residues $A_1$ and $A_2$, where present, (as referred to hereinbefore) and the terminal amino or methylamino and carboxy groups.

As regards derivativisation of groups in the cyclosporins and in the octapeptides, nonapeptides, decapeptides and undecapeptides, these derivatives may be of various forms including urethane derivatives of amino and methylamino groups, hydrazide, amide and particularly ester derivatives of carboxy groups, ester and ether derivatives of hydroxy groups and benzyl and suphityl derivatives of mercapto groups. In addition, an amino or methylamino group (particularly one present in a residue $A_1$ or $A_2$ as described hereinbefore) may be present in derivatised form as an acyl group R"CONH— or R"CONCH$_3$—, or R"SO$_2$NH— or R"SO$_2$NCH$_3$—, particularly one in which R" is hydrogen or an acyclic aliphatic hydrocarbon group such as $C_{1-6}$ alkyl and especially methyl as opposed to a cyclic aliphatic hydrocarbon or a heterocyclic or hydrocarbon aromatic group such as phenyl or substituted phenyl. Specific examples of such groups R" are formyl and acetyl. It may be stated however that the derivatives of most interest are those in which one or more of the various groups referred to hereinbefore are substituted by a protecting group conventionally used in peptide chemistry, for example benzyloxycarbonyl, t-butyloxycarbonyl and 9-fluorenylmethoxycarbonyl groups for the protection of amino and methylamino groups (as well as acyl groups), and the formation of t-butyl esters (and ethers in the latter case) for the protection of carboxy groups and hydroxy groups. Another form of derivativisation involves the formation of salts, particularly salts with a physiologically acceptable acid or base for in vivo use of the compounds, for example salts formed between an amino or methylamino group and an acid such as hydrochloric acid, methane sulphonic acid, isethionic acid, tartaric acid and other solubilising acids and salts formed between the carboxy group and a base such as an alkali metal hydroxide, for example sodium hydroxide, quaternary ammonium hydroxides and amines such as tris (tris represents 2-amino-2-hydroxymethylpropane 1,3-diol). Yet a further form of derivativisation involves the formation of a heavy metal complex. It will be appreciated that when such derivatives of the cyclosporins are employed in pharmaceutical compositions they may in some cases exhibit an effect by behaving as a prodrug which releases the corresponding non-derivatised cyclosporin in vivo.

Preferences among the octapeptides, nonapeptides, decapeptides and undecapeptides correspond to those described for the cyclosporins and specific examples of these peptides correspond to the specific cyclosporins described herein and also to those peptide compounds given in the Examples including the corresponding deprotected compounds, for example H-Sar-(Me)Leu-Val-(Me)Leu-Ala-(D)Ala-(Me)Leu-(Me)Leu-(Me)Val-OH and H-Abu-Sar-(Me)-Leu-Val-(Me)Leu-Ala-(D)Ala-(Me)Leu-(Me)Leu-(Me)Val-OH.

In building up the peptides the diphenylphosphinic acid mixed anhydride coupling method may conveniently be used in conjunction, for example, with N-terminal protection by a benzyloxycarbonyl group and carboxy and hydroxy group protection by a tertiary butyl group. The procedures employed utilise conventional techniques of peptide chemistry and are illustrated in the Examples. Derivatives may be formed by the use of conventional procedures described in the art, for example using standard reagents for the insertion of conventional protecting groups and by reaction with acids or bases to form salts and with heavy metal halides to form complexes. Following preparation of the linear undecapeptide this is cyclized by one of various standard procedures, that using the Castro reagent Bt-OP(NMe$_2$)$_3$$^+$PF$_6$$^-$ being of particular value. (Bt represents the benzotriazolyl anion present in this reagent.)

The present invention thus includes a process for the preparation of a cyclosporin in which the acyclic undecapeptide which corresponds to the cyclosporin cleaved between positions 1 and 11 is cyclized.

It has been found that the addition of successive amino acids or peptides in the form of the mixed anhydride with diphenylphosphinic acid is of particular value for the synthesis of peptides containing amino acids in which the nitrogen atom is substituted by a methyl group (or other aliphatic hydrocarbon group, for example one as described hereinbefore). The presence of a number of N-methylated amino acids among the residues $A_1$ to $A_{11}$ makes this technique of especial applicability in the synthesis of the octa-, nona-, deca- and undeca-peptides of the present invention. The technique has been found to result in very low levels of racemisation of the N-substituted amino acids as compared with other coupling procedures and generally to give particularly high yields of pure products.

The present invention thus includes a method for the coupling of a first amino acid N-substituted by an aliphatic hydrocarbon group or a first peptide containing such an amino acid, particularly at the C-terminus thereof, with a second amino acid or a second peptide in which the first acid or peptide is reacted in the form of a diphenylphosphinic acid mixed anhydride thereof with the amino group of the second amino acid or the terminal amino group of the second peptide. In such a method reactive groups such as the amino group of the first amino acid or the terminal amino group of the first peptide and the carboxy group of the second amino acid or the terminal carboxy group of the second peptide, and other free amino, carboxy and hydroxy groups, etc., will usually be in protected form.

The cyclosporins according to the present invention may be formulated for use as pharmaceuticals for both veterinary and particularly human use by a variety of methods. For instance, they may be applied as a composition, for example an aqueous, oily or emulsified composition, incorporating a liquid diluent which may often be employed in injectable form for parenteral administration and therefore may conveniently be sterile and pyrogen free. Oral administration may however also be used. Although compositions incorporating a liquid diluent may be used for oral administration, it is more usual to use compositions incorporating a solid carrier, for example a conventional solid carrier material such as starch, lactose, dextrin or magnesium stearate. Such solid compositions may conveniently be of a formed type, for example as tablets, capsules (including spansules), etc.

Other forms of administration than by injection or through the oral route may also be considered in both human and veterinary contexts, for example the use of suppositories or pessaries. Another form of pharmaceutical composition is one for buccal or nasal administration or alternatively drops for administration into the eye which may conveniently contain a sterile diluent.

Compositions may be formulated in unit dosage form, i.e. in the form of discrete portions containing a unit dose, or a multiple or sub-unit of a unit dose.

The undecapeptides of the present invention are of interest for use in various contexts in which known cyclosporins are used, for example as anti-bacterial agents or more particularly as immunosuppressive and anti-inflammatory agents, for example in organ transplantation and in the treatment of auto-immune disease and of rheumatoid arthritis. The compounds are of especial interest as potentially possessing an advantageous spectrum of activity as compared with the known cyclosporins. Thus, the known cyclosporins tend to exhibit disadvantageous effects in addition to the beneficial ones. There is therefore a need for compounds in which the beneficial effects are enhanced and/or the undesirable effects are reduced, which result can be achieved, inter alia, from an ability to use a compound at a lower dosage rate at which the former effects are substantially maintained whilst the latter are reduced. Whilst dosage levels may depend on the intended use, the mode of formulation and the particular compound (I) which is being used, it may be stated by way of guidance that a daily dose in the range of 1 to 100 or 500, particularly 20 to 80 mg/kg body weight is often appropriate, repeated if necessary in a daily regimen and/or in several separate treatments. It will be appreciated however that dosages below or above this range may be used where appropriate. In particular, dosage levels of as low as 0.1 or even 0.01 mg/kg may be considered, coupled with a preferred range of dosage of 0.1 to 10 mg/kg, for example 1 to 10 mg/kg, there being suggestions from in vitro data that the compounds may be of value at quite low doses.

The present invention thus includes a method of treating bacterial infections, inflammation or conditions requiring immunosuppressive treatment in patients which comprises administering to the patient a therapeutically effective amount of a compound (I) as defined hereinbefore.

The invention is illustrated by the following Examples of which Examples 1 and 2 relate to the synthesis of the same N- and C-terminally protected octapeptide by different routes, Example 3 relates to a N- and C-terminally protected nonapeptide and Example 4 to the same nonapeptide in C-terminally protected form. Examples 5 to 8 relate to N- and C-terminally protected decapeptides and Examples 9 to 12 relate to the same group of decapeptides in C-terminally protected form. Examples 13 to 23 relate to N- and C-terminally protected undecapeptides and Examples 24 to 38 relate to N-terminally protected and N- and C-terminally deprotected undecapeptides. Examples 39 to 46 relate to cyclic undecapeptides Example 47 relates to tests of activity of representative compounds of the invention and is illustrated by FIGS. 1a to 1e which are graphs showing $^3H$ thymidine uptake as a function of dosage of the compounds.

EXAMPLES

Solvents were dried and distilled prior to use, THF and DMF dried over $CaH_2$, the latter being distilled in vacuo, and stored over molecular sieves type 5A. Liquid chromatography separation was performed on a silica gel column using KIESELGEL (60–230 mesh ASTM) with a variety of solvent systems. HPLC was carried out using a SPECTRA PHYSICS SP8700 fitted with a 25×0.46 cm ODS CHROMOPAK C18 column eluting with $CH_3CN/H_2O$ gradients at a flow rate of 1.5 $cm^3$/min. Gel filtration was carried out using SEPHADEX LH20 or SEPHADEX G10 eluting with DMF and water respectively. Fractions were monitored by uv absorbance at 280 nm (UNICORD III) or by optical rotation (THORN-BENDIX 143D polarimeter). In some cases column eluant was also monitored by hplc at 230 nm.

Melting points were recorded on a KOFLER block and are uncorrected. Optical rotations were measured on a BENDIX type 153 automatic polarimeter (1 cm cell) using the sodium D line. I.R. spectra were determined using sodium chloride cells or rock salt flat plates on a PERKIN ELMER 1320spectrometer. $^1H$ N.m.r. spectra were recorded either on a PERKIN ELMER R34 (220 MHz) or a BRUKER WM250 (250 MHz) spectrometer. (The proton signals are assigned to the groups to which they are believed to correspond.) Mass spectra were recorded on a VG 7070E spectrometer using E.I., C.I., DCI and FAB (electron impact, chemical ionisation, direct chemical ionisation and fast atom bombardment, respectively) as ionisation systems.

The following standard abbreviations are used in the Examples: THF=tetrahydrofuran; DMF=dimethylformamide; DppCl=diphenylphosphinic acid; NMM=N-methylmorpholine; EtoAc=ethylacetate; DCM=dichloromethane; NB=nitrobenzyl; Z=benzyloxycarbonyl; $Bu^t$=tertiary butyl; DMAP=4-dimethylaminopyridine.

The various protected amino acids used as intermediates in the Examples are prepared as follows.

(1) N-Z protected, C-unprotected, N-unmethylated amino acids

The protected amino acids Z-Val-OH, Z-D-Ala-OH, Z-Ala-OH, Z-Sar-OH and Z-Abu-OH were prepared from the corresponding unprotected amino acids by the methods of Bergmann et al, Ber., 1932, 65, 1192 and Carter et al. "Organic Synthesis", ed Horning, J. Wiley, New York, 1955, 3, 167.

(2) N-Z protected, C-unprotected, N-methylated amino acids

Z-(Me)-Leu-OH and Z-(Me)Thr($Bu^t$)-OH were prepared from the corresponding N-Z protected, C-unprotected amino acids by the method of Cheung et al, Con. J. Chem. 1973, 51, 1915.

(3) N-Z protected, C-t-butylated, N-methylated amino acids

Z-(Me)Leu-$OBu^t$ and Z-(Me)Val-$OBu^t$ were prepared from the corresponding N-Z protected, C-unprotected N-methylated amino acids using the method of Anderson, J. Am. Chem. Soc., 1960, 82, 3359 and Roeske, Chem. Ind., 1959, 1221.

(4) H-(Me)Leu-$OBu^t$ and H-(Me)Val-$OBu^t$

Z-(Me)Leu-$OBu^t$ and Z-(Me)Val-$OBu^t$ were each dissolved in methanol and hydrogenolysed in the presence of 10% Pd/C catalyst for twenty-four hours. The catalyst was removed by filtration and the filtrate evaporated to give an oil which was subsequently purified by fractional distillation under (0.5 mmHg) to give the title compound in each case as an oil of b.p. 48° C. (yield 71%) and 44° C. (yield 89%) respectively.

(5) Z-(Me)Ser($Bu^t$)-OH

Z-Ser($Bu^t$)-OH (12 g, 407 mM) and methyl iodide (20 $cm^3$, 320 mM) were dissolved in freshly distilled THF (120 $cm^3$) at 0° C., and sodium hydride dispersion (5.28 g, 120 mM) was added cautiously with gentle stirring. The suspension, protected from the atmosphere by a drying tube was stirred at 4° C. for seventy hours and the reaction worked-up in the usual way. The title compound was obtained as an oil (12.07 g, 96%); $[\alpha]^{25}$ −4.1° (c 1.2, $CH_3OH$).

(6) Fmoc-(Me)Thr($Bu^t$)-OH

10% $Na_2CO_3$ (5 $cm^3$) was added to a solution of H-(Me)Thr($Bu^t$)-OH (2 g, 10.5 mM) in water, followed by dioxan (16 $cm^3$). The mixture was cooled to 0° C. and Fmoc.Cl (2.7 g, 10.5 mM) added over a period of forty minutes, while maintaining the pH at 8.7, by addition of 10% $Na_2CO_3$. The ice-bath was removed half an hour after the addition of Fmoc.Cl was completed, after which time it was poured into water (500 $cm^3$). After washing with ether (×3) the aqueous layer was cooled and acidified with 1M $KHSO_4$, extracted into EtOAc, washed with water and brine. Solvent evaporation gave a foam which was purified on a silica gel column eluting with EtOAc/$CH_2Cl_2$ 1:8. Evaporation of the appropriate fractions afforded the title compound as a white foam (2 g, 45%); m.p., 44°–46° C.; $[\alpha]^{20}$ +12.8° (c 1, $CH_3OH$).

(7) Boc-Dab(Fmoc)-OH (a) H-Dab(Fmoc)-OH

Cupric sulphate (1.4 g, 5.5 mM) in (5.5 $cm^3$) water was added to a stirred solution of H-Dab-OH.2HCl (2 g, 0.5 mM) and NaOH (0.8 g, 0.02 mM) in water (44 $cm^3$), and the resulting mixture stirred for one hour. 9-Fluorenyl succinimide carbonate (3.2 g) was then added dropwise with vigorous stirring and the resulting mixture stirred at room temperature for three days. The precipitate resulting was filtered, washed with water and dried. Excess ethylene diamine tetraacetic acid disodium salt was then added to one liter of boiling water, and the suspension kept at boiling point for ten minutes. The product was filtered, washed with water and dried in high vacuo over phosphorus pentoxide, (3.4 g, 94%), m.p., 166° C.

(b) Boc-Dab(Fmoc)-OH

H-Dab-(Fmoc)-OH (3.4 g, 0.01 mM) was added to a solution of $Na_2CO_3$ (0.7 g) in water (5.1 $cm^3$) and dioxan/water (20 $cm^3$/9.9 $cm^3$) and stirred with cooling (ice-salt bath). Di-tert-butyl carbonate (2.4 g, 11 mM) was then added and the mixture stirred at 0° C. for one hour and room temperature for twenty-two hours. Dioxane was then evaporated and the residue basified to pH 10 with aqueous $Na_2CO_3$. After extraction into EtOAc, to remove excess di-tert-butyl carbonate, the aqueous layer was acidified with 1M $KHSO_4$. Extraction into EtOAc, washing the organic layer with water and brine, drying ($MgSO_4$) and solvent evaporation gave a white solid. This was recrystallised from $Et_2O$ to give the title compound (2.2 g, 50%); m.p., 79°–80° C.; $[\alpha]^{20}$ −12.7° (c 1, $CH_3OH$).

(8) Z-Hyp($Bu^t$)-OH (a) Z-Hyp($Bu^t$)-ONB

Isobutylene (600 $cm^3$) and concentrated $H_2SO_4$ (6.6 $cm^3$) were added to a solution of Z-Hyp(OH)-ONB (65 g, 0.16 mol) in $CH_2Cl_2$ (660 $cm^3$). The butylation vessel was stoppered and the reaction mixture gently stirred for five days. The product was then washed with water and brine, after addition of 2M $Na_2CO_3$ (50 ml). Solvent evaporation gave a yellow oil, (30 g, 41%); $[\alpha]^{20}$ −18.3° (c, 1.2, $CH_3OH$).

(9) Z-Hyp($Bu^t$)-OH

2M NaOH (778 $cm^3$) was added to a solution of Z-Hyp($Bu^t$)-ONB (30 g, 0.07M) in acetone (527 $cm^3$) and water (132 $cm^3$), and the mixture stirred at room temperature for two and a half hours. The solvent was removed in vacuo and the residue washed with ether. The aqueous layers were cooled and acidified with 1M $KHSO_4$, and extracted with EtOAc. The organic layer was then washed with water and brine and dried over $Na_2SO_4$. Solvent evaporation gave a solid, which was recrystallised from ether/petroleum-ether, to give the title compound (18 g, 86%); m.p., 76°–78° C.; [α]$^{20}$ −29.1° (c 1, CH$_3$OH).

The following general procedures were employed in the Examples.

General tert-butylation of C-terminal carboxyl group and hydroxy side chain of amino acids The N-benzyloxycarbonyl-N-methyl amino acid (0.21 mol) was dissolved in dichloromethane (300 cm$^3$), in a pressure vessel containing concentrated H$_2$SO$_4$ (5 cm$^3$). The butylation vessel was cooled to −40° to −60° C., and condensed isobutylene gas (450 cm$^3$) was added with gentle stirring. The vessel was then sealed and the reaction mixture stirred at room temperature for five days. The vessel was then cooled to −10° C., the seal removed and excess isobutylene allowed to evaporate. The solution was allowed to reach 0° C. and then brought to pH 9 with sodium carbonate (25 g/150 cm$^3$ H$_2$O). The solvent was removed by evaporation and the oily residue was dissolved in ethyl acetate, washed successively with 1M NaHCO$_3$, and water and dried over anhydrous Na$_2$SO$_4$. Solvent evaporation gave the tert-butylated product which was generally purified by silica gel chromatography using a variety of solvent systems.

Coupling using the diphenylphosphinic mixed anhydride method

A solution of the N-protected amino acid (1.1 equiv.) and NMM (2 equiv.) in THF (2.4 mM/cm$^3$) was cooled to −20° C. and DppCl (1.1 equiv.) added. The reaction mixture was stirred for ten to twenty minutes at −20° C. and a pre-cool solution of the amino component (1 equiv.) in THF (2.4 mM/cm$^3$) added. The suspension was stirred for one to two hours at −20° C. and at ambient temperature for 24–48 hours. The solvent was evaporated and the residue taken up into ethyl acetate, washed successively with brine, 1M KHSO$_4$, 1M NaHCO$_3$ and water. The organic phase was dried over Na$_2$SO$_4$ and evaporated to give a residual oil or solid containing trace amounts of diphenyl phosphinic acid. Products were generally purified by silica gel chromatography using a variety of solvent systems.

EXAMPLE 1

Z-(Me)Leu-Val-(Me)Leu-Ala-D-Ala-(Me)Leu-(Me)-Leu-(Me)Val-OBu$^t$ (1) Z-(Me)Leu-Val-(Me)Leu-OH (a) Z-Val-(Me)Leu-OBu$^t$

Z-Val-OH (36.84 g, 0.14 mM) in THF (60 cm$^3$) was activated with DppCl (34.9 g, 0.14 mM) in THF (60 cm$^3$) and NMM (18.7 cm$^3$, 0.14 mM) and coupled with H-(Me)Leu-OBu$^t$ (24.3 g, 0.12 mM) in THF (60 cm$^3$) according to the general procedure. The mixture was stirred at −20° C. for one hour and room temperature for twenty-four hours. The solvent was evaporated and the residue worked up as described in the general method, final purification on silica gel eluting with EtOAc/DCM (κ) gave the title compound (51.2 g, 91%), m.p., 54°–56° C., [α]$^{23}$ −67° (c 1.0, CH$_3$OH). Calculated for C$_{24}$H$_{38}$N$_2$O$_5$: C, 66.33; H, 8.81; N, 6.45. Found: C, 66.36; H, 8.98; N, 6.46%; δH (220 MHz, CDCl$_3$), 0.91 (6H, m, —CH$_3$, (Me)Leu), 1.02 (6H, m, β-CH$_3$ Val), 1.45 (9H, s, OBu$^t$), 1.51–1.70 (2H, m, β-CH$_2$, (Me)Leu), 1.91–2.10 (2H, m, β-CH, Val, —CH, (Me)Leu), 3.05 (3H, s, N—CH$_3$), 4.51–4.61 (1H, m, α-CH, Val), 5.08 (2H, s, PhCH$_2$), 5.21–5.30 (1H, m, α-CH(Me)Leu), 5.63 (1H, d, N-H, Val) and 7.37 (5H, s, ArH), m/z (M+, DCI). R$_t$ 12.2 min.

(b) H-Val-(Me)Leu-OBu$^t$

Z-Val-(Me)-OBu$^t$ (38 g, 85 mM) in methanol (150 cm$^3$) was hydrogenolysed over 10% Pd/C (5 g) at atmospheric pressure for twenty-four hours. The catalyst was removed by filtration and the solvent evaporated to give a white foam (22.5 g, 93%). [α]$^{22}$ −25.3°, (c 1.0, CH$_3$OH); δ$_H$ (220 MHz, CDCl$_3$), 0.88–1.09 (12H, m, —CH$_3$, (Me)Leu, β-CH$_3$, Val), 1.45 (9H, s, OBu$^t$), 1.63–1.92 (3H, m, β-CH$_2$, —CH, (Me)Leu), 2.47 (1H, m, β-CH, Val), 2.97 (3H, s, N—CH$_3$), 3.80 (1H, m, α-C—H, Val), 5.38 (1H, t, α-C—H(Me)Leu), and 7.29 (2H, br., —NH$_2$), m/z 300 (M+, DCI).

(c) Z-(Me)Leu-Val-(Me)Leu-OBu$^t$

Z-(Me)Leu-OH (23.3 g, 84 mM) in THF (30 cm$^3$) was activated using DppCl (19.9 g, 84 mM) in THF (30 cm$^3$) and NMM (9.36 cm$^3$, 84 mM) and coupled to H-Val-(Me)Leu-OBu$^t$ (21 g, 70 mM) in THF (20 cm$^3$) according to the general coupling procedure, being stirred at −20° C. for one hour and at room temperature for twenty-four hours. The residue, after solvent evaporation was worked-up as described in the general method and purified by silica gel chromatography eluting with CH$_2$Cl$_2$/EtOAc (3:1). Evaporation of the appropriate fractions gave (4) as a colourless oil, (33.2 g, 85%), [α]$^{23}$ −3.4° (c 1.0, CH$_3$OH). Calculated for C$_{31}$H$_{51}$N$_3$O$_6$: C, 66.26; H, 9.15; N, 7.48. Found: C, 66.53; H, 9.25; N, 7.59%; δ$_H$ (220 MHz, CDCl$_3$), 0.69–1.12 (18H, m, —CH$_3$(Me)Leu, β-CH$_3$Val), 1.33 (9H, s, OBu$^t$), 1.64–1.91 (6H, m, β-CH$_2$, —CH (Me)-Leu), 2.05 (1H, m, β-C—H, (Me)Val), 2.87 (3H, s, N—CH$_3$), 3.03 (3H, s, N—CH$_3$), 4.71–4.79 (1H, m, α-CH Val), 5.15–5.25 (4H, m, PhCH$_2$, α-CH (Me)Leu), 6.61–6.70 (1H, br.s., N—H Val), and 7.38 (5H, s, ArH), m/z 561 (M+, DCI), R$_t$ 13.0 min.

(2) Z-Ala-D-Ala-(Me)Leu-(Me)Leu-(Me)Val-OBu$^t$ (a) Z-(Me)Leu-(Me)Val-OBu$^t$

Z-(Me)Leu-OH (22.26 g, 84 mM) in THF (25 cm$^3$) was activated with NMM (9.36 cm$^3$, 84 mM) and DppCl (19.92 g, 84 mM) in THF (25 cm$^3$), and coupled with H-(Me)Val-OBu$^t$ (13.09 g, 70 mM) in THF (25 cm$^3$), according to the general procedure, being stirred at −20° C. for one hour and at room temperature for twenty-four hours. Solvent evaporation gave a residue which was washed in the usual way, the resulting oil being purified on a silica gel column eluting with EtOAc/DCM (1:2). Evaporation of the appropriate fractions gave the title compound as a colourless oil (31.43 g, 81%), [α]$^{23}$ −141.8° (c 1.0, CH$_3$OH). Calculated for C$_{26}$H$_{42}$N$_2$O$_5$: C, 66.90; H, 9.00; N, 9.25. Found: C, 66.60; H, 9.05; N, 9.08; δ$_H$ (220 MHz, CDCl$_3$), 0.6–1.10 (12H, m, β-CH$_3$ (Me)Val, —CH$_3$ (Me)Leu), 1.42 (9H, s, OBu$^t$), 1.59–1.82 (3H, m, β-CH$_2$, —CH (Me)Leu), 2.20 (1H, m, β-C-H (Me)Val), 2.91 (3H, s, N-CH$_3$), 2.82–3.02 (3H, 2s, N—CH$_3$ Conf.), 4.29–4.80 (1H, d×d, α-CH (Me)Val), 5.02 (1H, m, α-CH (Me)Leu), 5.25 (2H, s, PhCH$_2$), and 7.61 (5H, s, ArH), m/z 448 (M+, DCI), R$_t$ 12.2 min.

(b) H-(Me)Leu-(Me)Val-OBu$^t$

Z-(Me)Leu-(Me)Val-OBu$^t$ (17.92 g, 0.04 mM) in methanol (100 cm$^3$) was hydrogenolysed in the presence of 10% Pd/C Catalyst (1 g) at atmospheric pressure, for twenty-four hours. The catalyst was removed by filtration and the solvent evaporated to give the title compound as an oily foam (11.07 g, 90%), [α]$^{23}$ −123.6° (c 1.0, CH$_3$OH), δH (220 MHz, CDCl$_3$), 0.84–1.10 (12H, m, β-CH$_3$ (Me)Val, —CH$_3$ (Me)Leu), 1.26 (3H, m, β-CH$_2$, —CH (Me)Leu), 1.42 (9H, s, OBu$^t$), 1.91 (1H, m, β-C-H (Me)Val), 2.29 (3H, s, N-CH$_3$), 2.60 (1H, br.s., NH), 3.02 (3H, s, N—CH$_3$), 3.4–3.58 (1H, d×d, α-C—H), and 3.80-4.9 (1H, d×d, α-C—H); m/z 314 (M+, DCI).

(c) Z-(Me)Leu-(Me)Leu-(Me)Val-OBu$^t$

Z-(Me)Leu-OH (10.04 g, 36 mM) in THF (10 cm$^3$) was activated with DppCl (8.52 g, 36 mM) in THF (10 cm$^3$) and NMM (4.08 cm$^3$, 36 mM) and coupled with H-(Me)Leu-(Me)Val-OBu$^t$ (9.42 g, 30 mM) in THF (10 cm$^3$) by the general DppCl method. The reaction mixture was stirred at −20° C. for two hours and at room temperature for twenty-four hours and worked-up as described in the general procedure. The residue obtained was purified by silica gel chromatography eluting with EtOAc/DCM (1:2). Solvent evaporation of the appropriate fractions gave the title compound as a sticky white foam (14.85 g, 83%), [α9$^{23}$ −173.5° (c 1.0, CH$_3$OH). Calculated for: C$_{32}$H$_{53}$N$_3$O$_6$: C, 66.73; H, 9.28; N, 7.29. Found: C, 66.86; H, 9.41; N, 7.53%; δ$_H$ (220 MHz, CDCl$_3$), 0.73–1.09 (18H, m, β-CH$_3$ (Me)Val, —CH$_3$ (Me)Leu), 1.48 (9H, s, OBu$^t$), 1.23–1.87 (6H, m, β-CH$_2$, —CH (Me)Leu), 2.18 (1H, m, β-CH (Me)Val), 2.82-2.85 (3H, s, N—CH$_3$ Conf.), 2.87 (8H, 2s, NCH$_3$), 4.15–4.76 (1H, d×d, α-CH (Me)Val), 5.03 (1H, t, α-CH (Me)Leu), 5.21 (2H, s, PhCH$_2$), 5.56 (1H, t, 60 -CH (Me)Leu), and 7.34 (5H, s, ArH); m/z 576 (M+1, FAB), R$_t$ 13.6 min.

(d) H-(Me)Leu-(Me)Leu-(Me)Val-OBu$^t$

Z-(Me)Leu-(Me)Leu-(Me)Val-OBu$^t$ (11.52 g, 20 mM) in methanol 1100 cm$^3$) was hydrogenolysed in the presence of 10% Pd/C catalyst for twenty-four hours. The solution, after removal of the catalyst by filtration, was evaporated to give the title compound as a sticky foam (7.84 g, 89%); δH (220 MHz, CDCl$_3$), 0.74–1.14 (18H, m, β-CH$_3$ (Me)Val, —CH$_3$ (Me)Leu), 1.45 (9H, s, OBu$^t$), 1.52-1.94 (6H, m, β-CH$_2$, —CH (Me)Leu), 2.19 (1H, m, β-CH (Me)Val), 2.48 (3H, s, N-CH$_3$), 3.10 (3H, s, N—CH$_3$), 3.12 (3H, s, N—CH$_3$), 3.88 (2H, m, α-CH), 4.79 (1H, d, α-CH), and 6.37 (1H, br.d., NH); m/z 442 (M+1, FAB).

(e) Z-D-Ala-(Me)Leu-(Me)Leu-(Me)Val-OBu$^t$

Z-D-Ala-OH (4.01 g, 18 mM) in THF (6 cm$^3$) was activated by DppCl (4.25 g, 18 mM) in THF (6 cm$^3$) and NMM (1.97 cm$^3$, 18 mM), and the resulting mixed anhydride coupled to H-(Me)Leu-(Me)Leu-(Me)Val-OBu$^t$ (6.61 g, 15 mM) in THF (6 cm$^3$). After stirring at −20° C. for two hours and at ambient temperature for thirty hours the residue was worked-up as described in the general DppCl procedure and purified by silica gel chromatography eluting with EtOAc/DCM (1:2). Solvent evaporation of the appropriate fractions gave the title compound as a colourless oil, (6.8 g, 80%); [α]$^{24}$ −137.7° (c 1.0, CH$_3$OH). Calculated for: C$_{35}$H$_{58}$N$_4$O$_7$: C, 64.90; H, 9.04; N, 8.66. Found: C, 65.00; H, 9.02; N, 8.67%; δ$_H$ (220 MHz, CDCl$_3$), 0.73–1.11 (18H, m, β-CH$_3$ (Me)Val, —CH$_3$ (Me)Leu), 1.35 (3H, d, CH$_3$ D-Ala), 1.42 (9H, s, OBu$^t$), 1.48-1.82 (6H, m, β-CH$_2$, —CH (Me)Leu), 2.17 (1H, m, β-CH (Me)Val), (2.78-2.98 (6H, 4s, NCH$_3$ Conf.), 3.02 (3H, s, N—CH$_3$), 4.69 (1H, d×d, α-CH D-Ala) 4.74 (1H m, α-CH (Me)Val), 5.11 (2H, s, PhCH$_2$—), 5.03-5.66 (2H, m, 60 -CH (Me)Leu, 5.72 (1H, d, NH-D-Ala), and 7.39 (5H, s, ArH); m/z 646 (M+, DCI), R$_t$ 13.0 min.

(f) H-D-Ala-(Me)Leu-(Me)Leu-(Me)Val-OBu$^t$

Z-D-Ala-(Me)Leu-(Me)Leu-(Me)Val-OBu$^t$ (6.42 g, 10 mM) in methanol (50 cm$^3$) was hydrogenolysed in the presence of 10% Pd/C catalyst for twenty-four hours. The catalyst was removed by filtration and the filtrate evaporated to give the title compound as a sticky white foam, (4.76 g, 93%); [α]$^{25}$ −126° (c 1.2, CH$_3$OH); δ$_H$ (220 MHz, CDCl$_3$), 0.77–1.11 (18H, m, β-CH$_3$ (Me)-Val, —CH$_3$ (Me)Leu), 1.16-1.27 (3H, d, CH$_3$-D-Ala), 1.15 (9H, s, OBu$^t$), 1.34–1.83 (6H, m, β-CH$_2$, —CH (Me)Leu), 2.07 (2H, br.s., —NH$_2$), 2.18 (1H, m, β-CH (Me)Val), 2.87, 2.94, 3.01 (9H, series of singlets, N—CH$_3$), 3.8-3.99(1H, q, α-CH D-Ala), 4.72 (1H, d, α-CH (Me)Val), and 4.55 (2H, 2t, α-CH (Me)Leu); m/z 512 (M+1, FAB).

(g) Z-Ala-D-Ala-(Me)Leu-(Me)Leu-(Me)Val-OBu$^t$

Z-Ala-OH (2.40 g, 10.8 mM) in THF (4 cm$^3$) was activated using DppCl (2.55 g. 10.8 mM) in THF (4 cm$^3$) and NMM (1.2 cm$^3$, 10.8 mM) and coupled to H-D-Ala-(Me)Leu-(Me)Leu-(Me)Val-OBu$^t$ (4.68 g, 9 mM) in THF (4 cm$^3$) according to the standard procedure. The reaction mixture was stirred at −20° C. for one hour and at ambient temperature for twenty-four hours. The residue obtained after work-up by the general method was purified by silica gel chromatography using CH$_2$Cl$_2$/EtOAc (2:1) as eluant. Evaporation of the appropriate fractions gave the title compound as a white solid (5.18 g, 88%); m.p., 52°-53° C.; [α]$^{23}$ −168° (c 1.1, CHCl$_3$). Calculated for C$_{38}$H$_{63}$N$_5$O$_5$: C, 63.55; H, 8.86; N, 9.75. Found: C, 63.34; H, 8.96; N, 9.97%; δ$_H$ (220 MHz, CDCl$_3$), 0.76–1.04 (18H, m, β-CH$_3$ (Me)Val, —CH$_3$— (Me)Leu), 1.31 (3H, d, CH$_3$-D-Ala), 1.39 (3H, d, CH$_3$-L-Ala), 1.46 (9H, s, OBu$^t$), 1.49-1.98 (6H, m, β-CH$_2$, —CH (Me)Leu), 2.19 (1H, m, β-CH (Me)Val), 2.79-3.03 (9H, series of singlets, N-CH$_3$), 4.31 (1H, m, α-CH-L-Ala), 4.74 (1H, d×d, α-CH (Me)Val), 4.85 (1H, m, α-CH-D-Ala), 5.07 (2H, s, PhCH$_2$), 5.49–5.56 (2H, m, α-CH (Me)Leu), 5.66 (1H, d, NH-D-Ala), 7.07 (1H, d, NH-L-Ala), and 7.30 (5H, s, ArH); m/z 717 (M+1, FAB), R$_t$ 13.0 min.

(3) Z-(Me)Leu-Val-(Me)Leu-Ala-D-Ala-(Me)Leu-(Me)-Leu-(Me)Val-OBu$^t$

Z-(Me)Leu-Val-(Me)Leu-OH (0.25 g, 0.44 mM) in THF (6 cm$^3$) was activated using DppCl (0.15 g, 0.60 mM) in THF (5 cm$^3$) and NMM 0.07 cm$^3$, 0.60 mM) and coupled to H-Ala-D-Ala-(Me)Leu-(Me)Leu-Me)Val-OBu$^t$(0.27 g, 0.45 mM) in THF (5 cm$^3$) according to the general DppCl coupling method. The reaction mixture was stirred at 0° to −5° C. for one hour and at room temperature for forty-two hours. The residue, after solvent evaporation was applied to a SEPHADEX LH20 column eluting with DMF. Evaporation of the appropriate fractions gave the title compound as a white foam (0.13 g, 27%); m.p., 65°-67° C.; [α]$^{20}$ −134° C. (c 1.0, CH$_3$OH). Calculated for C$_{57}$H$_{98}$N$_8$O$_{11}$: C, 63.87; H, 9.22; N, 10.48. Found: C, 63.59; H, 9.29; N, 10.33; δ$_H$ (250 MHz, CDCl$_3$), 0.77-1.03 (36H, m, β-CH$_3$ of Val, (Me)Val, —CH$_3$ of (Me)Leu), 1.15 (3H, d, CH$_3$ D-Ala), 1.36 (3H, d, CH$_3$-L-Ala), 1.44 (9H, s, OBu$^t$), 1.47-1.52 (8H, m, β-CH$_2$ (Me)Leu), 1.84-2.40 (6H, m, β-CH Val, β-CH (Me)Val, —CH (Me)Leu), 2,79-3.06 (15H, series of singlets N-CH$_3$), 4.39-5.03 (6H, α-CH (Me)Val, Val, Ala, D-Ala (Me)Leu), 5.17 (2H, s, PhCH₂), 5.48–5.50 (2H, m, α-CH (Me)Leu), 6.65 (1H, d, NH-D-Ala), 6.90 (1H, d, NH-Val), 7.15 (1H, br.s., NH L-Ala) and 7.26 (5H, s, ArH); m/z 1.73 (M+1, FAB); Rt 13.6 min.

EXAMPLE 2

Z-(Me)Leu-Val-(Me)Leu-Ala-D-Ala-(Me)Leu-(Me)-Leu-(Me)Val-OBu$^t$ (1) H-L-Ala-D-Ala-(Me)Leu-(Me)Leu-(Me)Val-OBu$^t$

Z-Ala-D-Ala-(Me)Leu-(Me)Leu-(Me)Val-OBu$^t$ (29.86 g, 50 mM; prepared as described in Example 1) was dissolved in methanol (200 cm³) and hydrogenolysed in the presence of 10% Pd/C catalyst (2.7 g), at atmospheric pressure for twenty-four hours. The catalyst was removed by filtration and the filtrate evaporated to give the title compound as a foam, (23.6 g, 95%); m.p., 70°–71° C.; [α]$^{24}$ – 195.4° (c 1.2, CH₃OH); δ$_H$(220 MHz, CDCl₃), 0.76–1.09 (18H, m, β-CH₃ (Me)Val, —CH₃ (Me)Leu), 1.22 (3H, d, CH₃-D-Ala), 1.36 (3H, d, CH₃ Ala), 1.45–1.48 (9H, 2s, OBu$^t$ Conf.), 1.54–2.09 (6H, m, β-CH₂, —CH (Me)Leu), 2.20 (1H, m, β-CH (Me)Val), 2.83–3.03 (9H, series of singlets, N-CH₃), 3.58 (1H, br.s., NH D-Ala), 3.75–3.86 (1H, d×d, α-CH (Me)Val), 4.72–4.90 (2H, m, α-CH Ala, D-Ala), 5.56 (2H, 2t, α-CH (Me)Leu), and 7.33–7.89 (2H, br.m., —NH₂); m/z 583 (M+1, FAB).

(2)
Z-(Me)Leu-Ala-D-Ala-(Me)Leu-Leu-(Me)Val-OBu$^t$

Z-(me)Leu-OH (16.65 g, 59.7 mM) in THF (40 cm³) was activated using DppCl (14.1 g, 59.7 mM) in THF (40 cm³) and NMM (5.46 cm³, 59.7 mM) and coupled to H-Ala-D-Ala-(Me)Leu-(Me)Leu-(me)Val-OBu$^t$ (29 g, 49.7 mM) in THF (30 cm³); according to the general procedure. The reaction mixture was stirred at −20° C. for three hours and at ambient temperature for thirty hours. The reaction was worked-up as described for the general DppCl method, and the residue obtained was purified on a silica gel column eluting with CH₂Cl₂/EtOAc (2:1). Solvent evaporation of the appropriate fractions gave the title compound as a white solid (36.1 g, 96%); m.p., 47°–48° C.; [α]$^{25}$ – 173° (c 1.0, CH₃OH). Calculated for C₄₅H₇₆N₆O₉: C, 63.91; H, 9.10; N, 9.95; Found: C, 64.12; H, 9.32; N, 9.80%; δ$_H$ (250 MHz, CDCl₃), 0.76–1.03 (24H, β-CH₃ (Me)Val, —CH₃ (Me)Leu), 1.25–1.34 (6H, d×d, CH₃ D-Ala, Ala), 1.44 (9H, s, OBu$^t$), 1.77 (3H, m, —CH (Me)Leu), 1.58–1.85 (6H, m, β-CH₂ (Me)Leu), 2.17 (1H, m, β-CH (Me)Val), 2.77–3.00 (9H, series of singlets, —NCH₃), 4.39 (1H, t, α-CH L-Ala), 4,71 (1H, d, α-CH (Me)Val), 4.63–4.87 (2H, m, α-CH D-Ala, (Me)Leu), 5.14 (2H, s, PhCH₂), 5.39–5.50 (2H, m, α-CH (Me)Leu), 6.57 (1H br.d., NH-D-Ala), 6.88 (1H, br.s., NH-L-Ala), and 7.38 (5H, s, ArH); m/z 844 (M+, DCI), R$_t$ 13.0 min.

(3)
H-(Me)Leu-Ala-D-Ala-(Me)Leu-(Me)Leu-(Me)Val-OBu$^t$

Z-(Me)Leu-Ala-D-Ala-(Me)Leu-(Me)Leu-(Me)Val-OBu$^t$ (35.8 g, 42.4 mM) in methanol (200 cm³) was hydrogenolysed in the presence of 10% Pd/C catalyst at one atmosphere for thirty hours. The catalyst was removed by filtration and the filtrate evaporated to give the title compound as a white foam, (28.3 g, 94%), m.p., 50°–52° C.; [α]$^{25}$ – 155.4° (c 1.2, CH₃OH). Calculated for C₃₇H₇₀N₆O₆: C, 62.39; H, 9.93; N, 11.82. Found: C, 61.98; H, 9.79; N, 11.88%; δ$_H$ (250 MHz, CDCl₃), 0.76–1.03 (24H, m, β-CH₃ (Me)Val, —CH₃ (Me)Leu, 1.24–1.36 (6H, d×d, CH₃ Ala, D-Ala), 1.45 (9H, s, OBu$^t$), 1.58–1.90 (6H, m, β-CH₂ (Me)Leu), 1.98 (3H, m, —CH (Me)Leu). 2.17 (1H, m, β-CH (Me)Val). 2.76–2.99 (12H, series of singlets, —NCH₃), 4.03 (1H, br,d., —NH-(Me)Leu), 4.44–5.50 (5H, m, α-CH), 6.26 (1H, br.d., NH-Ala), 8.39 (1H, br.d., NH-D-Ala); m/z 710 (M+, DCI).

(4)
Z-(Val-(Me)Leu-Ala-D-Ala-(Me)Leu-(Me)Leu-(Me)-Val-OBu$^t$

Z-Val-OH (11.45 g, 45.6 mM) in THF (30 cm³) was activated using DppCl (10.79 g, 45.6 mM) in THF (30 cm³) and NMM (5.0 cm³, 45.6 mM) and the resulting mixed anhydride coupled to H-(Me)Leu-Ala-D-Ala-(me)Leu-Me)Leu-(Me)Val-OBu$^t$ (27 g, 38 mM) in THF (30 cm³), as described for the general DppCl coupling procedure. The reaction mixture was stirred at −20° C. for two hours and at room temperature for forty-five hours. The reaction was worked-up as described in the general procedure and the residue subjected to chromatography on silica gel eluting with CH₂Cl₂/EtOAc (2:1). Evaporation of the solvent gave the title compound as a white foam, (26.9 g, 75%), m.p., 69.5° C.; [α]$^{25}$ – 143.1° (c 1.1 CH₃OH). Calculated for C₅₀H₈₅N₇O₁₀: C, 63.58; H, 9.08; N, 10.38. Found: C, 63.36; H, 9.05; N, 10.48%; δ$_H$ (250 MHz, CDCl₃), 0.71–1.06 (30H, m, β-CH₃ Val, (Me)Val, —CH₃ (Me)-Leu), 1.31–1.34 (6H, d×d, CH₃ Ala, D-Ala), 1.44 (9H, s, OBu$^t$), 147–1.60 (3H, m, —CH (Me)Leu), 1.58–1.84 (6H, m, β-CH₂ (Me)Leu, 1.99 (1H, m, β-CH Val), 2.14 (1H, m, β-CH (Me)Val), 2.76–3.01 (12H, series of singlets —NCH₃), 4.36 (1H, m, α-CH Ala), 4.46 (1H, m, α-CH Val), 4.68 (1H, d, α-CH (Me)Val), 4.61–4.84 (1H, m, α-CH D-Ala), 5.03–5.13 (4H, m, PhCH₂, α-CH (Me)Leu), 5.34–5.45 (2H, m, α-CH (Me)Leu), 6.58 (1H, br.d., NH-D-Ala), 6.82–7.01 (2H, br.m., NH-L-Ala, Val), and 7.23 (5H, s, ArH); m/z 943 (M+, DCI); R$_t$ 13.6 min.

(5)
H-Val-(Me)Leu-Ala-D-Ala-(Me)Leu-(Me)Leu-(Me)-Val-OBu$^t$

Z-Val-(Me)Leu-Ala-D-Ala-(Me)Leu-(Me)Leu-(Me)-Val-OBu$^t$ (26 g, 27.5 mM) in methanol (100 cm³) was hydrogenolysed in the presence of 10% Pd/C catalyst for two days. Evaporation of the solvent, after removal of the catalyst, gave the title compound as a white foam, (20.96 g, 94%); m.p., 71°–72° C.; [α]$^{24}$ – 138.9° (c 1.2, CH₃OH). Calculated for C₄₂H₂₉N₇O₈: C, 62.25; H, 9.84; N, 12.10. Found: C, 62.20; H, 9.65; N, 12.23%; δ$_H$ (250 MHz, CDCl₃), 0.71–1.06 (30H, m, —CH₃ (Me)Leu, β-CH₃ Val, (Me)Val), 1.23–1.33 (6H, 2d, CH₃-Ala, D-Ala), 1.44 (9H, s, OBu$^t$), 1.40–1.61 (3H, m, —CH (Me)Leu), 1.50–1.84 (6H, m, β-CH₂ (Me)Leu), 1.25–1.99 (2H, m, β-CH Val, (Me)Val), 2.11 (2H, br., —NH₂), 2.78–3.01 (12H, series of singlets —NCH₃), 4.38 (1H, m, α-CH Ala), 4.45–5.44 (6H, α-CH (Me)Leu, (Me)Val, Val, D-Ala), 6.68 (1H, br.d., NH-D-Ala), and 6.95 (1H, br.d., NH-L-Ala); m/z 909 (M+, DCI).

(6)
Z-(Me)Leu-Val-(Me)Leu-L-Ala-D-Ala-(Me)Leu-(Me)-Leu-(Me)Val-OBu$^t$

Z-(Me)Leu-OH (8.56 g, 30.7 mM) in THF (10 cm³) was activated using DppCl (7.26 g, 30.7 mM) in THF (10 cm$^3$) and NMM 3.37 cm$^3$, 30.7 mM) and was coupled to H-val-(Me)Leu-Ala-D-Ala-(Me)Leu-(Me)Leu-(Me)Val-OBu$^t$ (20.7 g, 25.6 mM) in THF (50 cm$^3$), according to the general coupling procedure. The reaction mixture was stirred at $-20°$ C. for two hours and at ambient temperature for forty-five hours. The solvent was evaporated and the reaction worked-up as described in the general procedure. The residue was subjected to chromatography on silica gel eluting with EtOAc/CH$_2$Cl$_{12}$ (1:1). Evaporation of the appropriate fractions gave the title compound as a white solid, (23 g, 94%); m.p., 75° C.; [α]$^{24}$ −133.1° (c 1.2, CH$_3$OH). Calculated for C$_{57}$H$_{98}$N$_8$O$_{11}$: C, 63.87; H, 9.22; N, 10.48; Found: C, 63.74; H, 9.23; N, 10.33%; δ$_H$ (250 MHz, CDCl$_3$, 0.76–1.04 (36H, m, β-CH$_3$ Val, (Me)Val, —CH$_3$ (Me)Leu), 1.31–1.34 (6H, d×d, CH$_3$ Ala, D-Ala), 1.44 (9H, s, OBu$^t$), 1.47–1.60 (3H, m, —CH(Me)-Leu), 1.61–1.70 (8H, m, β-CH$_2$ (Me)Leu), 1.98 (1H, m, β-CH Val), 2.15 (1H, m, β-CH (Me)Val), 2.79–3.06 (15H, series of singlets, NCH$_3$), 4.39–4.49 (1H, m. α-CH Ala), 4.69–4.95 (3H, m, α-CH D-Ala, Val, (Me)Val), 5.03–5.23 (4H, m, α-CH (Me)Leu, PhCH$_2$), 5.29–5.52 (2H, m, α-CH (Me)Leu), 6.50 (1H, br.d., NH-D-Ala), 6.51 (1H, br.d., NH Val), 6.84 (1H, br.d., NH-L-Ala), and 7.28 (5H, s, ArH); m/z 1070 (M+, DCI), R$_t$ 13.6 min.

EXAMPLE 3

Z-Sar-(Me)Leu-Val-(Me)Leu-Ala-D-Ala-(Me)Leu-(Me)Leu-(Me)Val-OBu$^t$

Z-Sar-OH (16.56 9, 74.28 mM) in THF (24 cm$^3$) was activated using DppCl (17.55 g, 74.28 mM) in THF (24 cm$^3$) and NMM (7.13 cm$^3$, 74.28 mM) at $-20°$ C. and coupled to H-(Me)Leu-Val-(Me)Leu-Ala-D-Ala-(Me)Leu-(Me)Leu-(Me)Val-OBu$^t$ (57.66 g, 61.89 mM) in THF (60 cm$^3$) as described for the general DppCl method. The reaction mixture was stirred at $-15°$ C. for two hours and at ambient temperature for forty-five hours, and was worked-up in the usual way. The residue was purified on a silica gel column eluting with EtOAc/CH$_2$Cl$_2$ (1:1) to give the title compound as a white solid, (45.36 g, 64%); m.p., 64° C.; [α]$^{24}$ −131.5° C. (c 1.1, CH$_3$OH). Calculated for C$_{60}$H$_{103}$N$_9$O$_{12}$: C, 63.09; H, 9.09; N, 11.03. Found: C, 63.11; H, 9.14; N, 10.88%; δ$_H$ (250 MHz, CDCl$_3$ 2 Confs.), 0.76–1.06 (36H, m, β-CH$_3$, Val, (Me)Val, γ-CH$_3$ (Me)Leu), 1.27–1.36 (6H, d×d, CH$_3$, Ala, D-Ala), 1.44 (9H, s, OBu$^t$), 1.52–1.87 (12H, m, β-CH$_2$, —CH (Me)Leu), 2.04–2.17 (2H, m, β-CH, Val, (Me)Val), 2.80–3.07 (18H, series of s, N-CH$_3$), 4.01–4.11 (2H, d×d, CH$_2$, Sar), 4.36 (1H, α-CH, Ala), 4.65–4.72 (2H, m, α-CH, Val, (Me)Val), 4.68–5.07 (3H, m, α-CH, D-Ala, (Me)Leu), 5.12 (2H, s, Ph-CH$_2$—), 5.45 (2H, m, α-CH, (Me)Leu), 6.50 (1H, br.d., NH, D-Ala), 6.63 (1H, br.d., NH, Val), 6.82 (1H, br.d., NH-Ala), 7.31 (5H, s, ArH); m/z 1141 (M+, DCI), R$_t$ 12.0 min.

EXAMPLE 4

H-Sar-(Me)Leu-Val-(Me)Leu-Ala-D-Ala-(Me)Leu-(Me)Leu-(Me)Val-OBu$^t$

Z-Sar-(Me)Leu-Val-(Me)Leu-Ala-D-Ala-(Me)Leu-(Me)Leu-(Me)Val-OBu$^t$ in methanol (150 cm$^3$) was hydrogenolysed at atmospheric pressure in the presence of 10% Pd/C catalyst for twenty-four hours. The catalyst was removed by filtration and the solvent evaporated to dryness. The residue was triturated with ether to afford the title compound as a white solid, (12.8 g, 97%); m.p., 96°–97° C.; [α]$^{23}$ −154.2° (c 1, CH$_3$OH). Calculated for C$_{52}$H$_{97}$N$_9$O$_{10}$: C, 61.19; H, 9.70; N, 12.50. Found: C, 61.56; H, 9.73; N, 12.02%; δ$_H$ (250 MHz, CDCl$_3$), 1.04–1.76 (36H, m, γ-CH$_3$, (Me)Leu; β-CH$_3$, Val, (Me)Val), 1.29–1.46 (6H, d×d, CH$_3$, Ala, D-Ala), 1.43 (9H, s, OBu$^t$), 1.52–1.86 (12H, m, β-CH$_2$, γ-CH, (Me)Leu), 2.15–2.45 (3H, m, β-CH Val, (Me)Val, -NH-Sar), 2.74–3.09 (18H, series of s, N-CH$_3$), 4.32–4.37 (2H, d×d, CH$_2$-Sar), 4.34 (1H, m, α-CH, Ala), 4.51–5.52 (7H, m, α-CH), 6.59 (1H, br.d., NH, D-Ala), 6.72 (1H, br.d., NH-Val), and 6.84 (1H, br.d., NH-Ala); m/z 1007 (M+, DCI).

EXAMPLE 5

Z-Abu-Sar-(Me)Leu-Val-(Me)Leu-Ala-D-Ala-(Me)Leu-(Me)Leu-(Me)Val-OBu$^t$

Z-Abu-OH (4.4 g, 18.8 mM) in THF (8 cm$^3$ was activated using DppCl (4.5 g. 18.8 mM) in THF (5 cm$^3$) and NMM (2.1 g, 18.8 mM) at $-20°$ C. and coupled to H-Sar-(Me)Leu-Val-(Me)Leu-Ala-D-Ala-(Me)Leu-(Me)Leu-(Me)Val-OBu$^t$ (12.8 g, 15.7 mM; prepared as described in Example 4) according to the general DppCl procedure. The reaction mixture was stirred at $-15°$ C. for two hours and at ambient temperature for forty-five hours. The reaction was worked-up as described in the usual way and the residue purified on a silica gel column eluting with EtOAc/DCM (1:2). Evaporation of the appropriate fractions gave the title compound as a white foam, (14.1 g, 90%); m.p., 83°–84° C.; [α]$^{24}$ −168.2° (c 1.1, CH$_3$OH). Calculated for C$_{64}$H$_{110}$N$_{10}$O$_{13}$: C, 62.58; H, 9.02; N, 11.40. Found: C, 62.29; H, 9.09; N, 11.28%; δ$_H$ (250 MHz, CDCl$_3$, 2 Confs.), 0.75–1.06 (39H, m, β-CH$_3$-Val, (Me)Val, γ-CH$_3$-(Me)Leu, β-CH$_3$-Abu), 1.25–1.35 (6H, d×d CH$_3$-Ala, D-Ala), 1.48 (9H, s, OBu$^t$), 1.53–1.86 (12H, m, β-CH$_2$, γ-CH-(Me)Leu), 1.91 (2H, m, β-CH$_2$-Abu), 2.02–2.15 (2H, m, β-CH-Val, (Me)Val), 2.66–3.26 (18H, series of s, N-CH$_3$), 4.26–4.30 (2H, d×d, CH$_2$-Sar), 4.35 (1H, m, α-CH-Ala), 4.50–4.90 (3H, m, α-CH-(Me)Val, D-Ala, Val), 4.94–5.07 (3H, m, α-CH-Abu and (Me)Leu), 5.08 (2H, s, Ph-CH$_2$—), 5.46 (2H, m, α-CH-(Me)Leu), 5.90 (1H, br.d., NH-D-Ala), 6.55 (1H, br.d., NH-Val), 6.71 (1H, br.d., NH-Ala), and 7.33 (5H, s, ArH); R$_t$ 13.2 min.; m/z 1225 (M+, DCI).

EXAMPLE 6

Z-Thr(Bu$^t$)-Sar-(Me)Leu-Val-(Me)Leu-Ala-D-Ala-(Me)Leu-(Me)Leu-(Me)Val-OBu$^t$

NMM (1.1 cm$^3$, 9.9 mM, 2.5 equiv.) was added to a stirred solution of Z-Thr(Bu$^t$)-OH (1.4 g, 4.4 mM, 1 equiv.) in THF (10 cm$^3$) and the mixture stirred at $-20°$ C. DppCl (1.4 g, 6 mM, 1.5 equiv.) in THF (4 cm$^3$) was then added and the resulting mixture stirred at $-20°$ C. for twenty minutes.

A pre-cooled solution of H-Abu-Sar-(Me)Leu-Val-(Me)Leu-Ala-D-Ala-(Me)Leu-(Me)Leu-(Me)Val-Obu$^t$ (4 g, 4 mM, 1 equiv.; prepared as described in Example 4) in THF (10 cm$^3$) was then added and the reaction mixture stirred at $-20°$ C. for one hour, 0°–5° C. for one hour and room temperature for four days. The product was worked-up as described for the general DppCl procedure, to yield an oil which was purified on a silica gel column eluting with EtOAc. Evaporation of the appropriate fractions gave the title compound as a white foam, (2.5 g, 48%); m.p., 85° C; [α]$^{20}$ −159.5° (c 1, CH$_3$OH). Calculated for C$_{68}$H$_{118}$N$_{10}$O$_{14}$: C, 62.87; H, 9.09; N, 10.79. Found: C, 62.48 ; H, 9.26; N, 10.71%; δ$_H$ (250 MHz, CDCl$_3$) 0.78–1.07 (36H, m, CH$_3$ of (Me)Val, (Me)Leu, Val), 1.13 (3H, d, β-CH₃ of Thr), 1.21 (9H, s, Thr, OBuᵗ), 1.28-1.38 (6H, m, CH₃ of Ala, D-Ala), 1.44 (9H, s, (Me)Val, OBuᵗ), 1.52-1.83 (10H, m, β-CH₂ of (Me)Leu and Abu), 1.85-2.32 (6H, m, β-CH of (Me)-Val, Val and γ-CH of (Me)Leu), 2.80-3.09 (18H, series of s, N-CH₃), 3.35 (1H, d, α-CH, Sar), 3.45-3.50 (1H, m, β-CH of Thr), 4.41-4.52 (1H, m, α-CH, Ala), 4.70-4.92 (7H, m, α-CH), 5.20 (1H, d, α-CH, Thr), 5.14 (2H, s, Ph-CH₂), 5.31-5.56 (2H, m, α-CH), 6.21 (1H, d, NH-Thr), 6.50 (1H, d, NH-D-Ala), 6.92-7.02 (2H, m, NH-Val, L-Ala), 7.35 (5H, s, ArH); m/z 1298 (M⁺, CI), R$_t$ 14.1 min.

EXAMPLE 7

Z-Nva-Sar-(Me)Leu-Val-(Me)Leu-Ala-D-Ala-(Me)-Leu-(Me)Leu-(Me)Val-OBuᵗ

Z-Nva-OH (1.79 b, 7.14 mM) in THF (5 cm³) was activated using DppCl (2.11 g, 8.92 mM) in THF (5 cm³) and NMM (1.30 cm³, 8.92 mM) at −20° C. and coupled to H-Sar-(Me)Leu-Val-(Me)Leu-Ala-D-Ala-(Me)Leu-(Me)Leu-(Me)Val-OBuᵗ (6.10 g, 5.95 mM; prepared as described in Example 4) as described in the general DppCl method. The reaction mixture was stirred at −20° C. for two hours and at ambient temperature for thirty-six hours, and the residue worked-up in the usual way. Purification on a silica gel column eluting with EtOAc/DCM (2:1) gave the title compound as a white foam, (6.4 g. 86%); m.p., 85°-86° C.; [α]²⁴ −164°, (c 1, CH₃OH). Calculated for C₆₅H₁₁₂N₁₀O₁₃: C, b2.85; H, 9.10; N, 11.28. Found: C, 62.69; H, 9.21; N, 10.94%; δ$_H$ (250 MHz, CDCl₃, 2 Confs.). 0.77-1.03 (39H, m, β-CH₃-(Me)Val, Val, γ-CH₃(Me)Leu, CH₃-Nva), 1.29-1.31 (10H, d×d, CH₃-Ala, D-Ala, β, -CH₂-Nva), 1.44 (9H, s, OBuᵗ) 1.51-1.81 (12H, m, β-CH₂, γ-CH of (Me)Leu), 2.05-2.24 (2H, m, β-CH-Val, (Me)Val), 2.70; 3.28 (18H, series of s, N-CH₃), 4.28-4.35 (2H, d×d, CH₂-Sar), 4.35 (1H, m, α-CH-Ala), 4.38 (1H, t, α-CH-Nva), 4.66-5.06 (4H, m. α-CH), 5.10 (2H, s, PhCH₂), 5.46-5.52 (2H, m, α-CH-(Me)Leu), 5.89-5.92 (1H, br.d., NH-Nva), 6.58 (1H, br.d., NH-D-Ala), 6.78 (1H, br.d., NH-Val), 6.80-6.95 (1H, br.d., NH-Ala), and 7.34 (5H, s, ArH), R$_t$ 13.8 min.; m/z 1241 (M⁺, DCI).

EXAMPLE 8

Z-Nle-Sar-(Me)Leu-Val-(Me)Leu-Ala-D-Ala-(Me)-Leu-(Me)Leu-(Me)Val-OBuᵗ

Z-Nle-OH (1.4 g, 5.2 mM) in THF (5 cm³) was activated using DppCl (1.5 g, 6.2 mM) in THF (5 cm³) and NMM (1.1 g, 10.4 mM) at −20° C. and coupled to H-Sar-(Me)Leu-(Val-(Me)Leu-Ala-D-Ala-(Me)Leu-(Me)Leu-(Me)Val-OBuᵗ (4.8 g, 4.7 mM) as described in the general DppCl coupling procedure. The reaction mixture was stirred at −20° C. for two hours and at room temperature for forty-six hours. After work-up as described in the general DppCl procedure, the residue was purified on a silica gel column eluting with EtOAc/DCM (3:1), to give the title compound as a white solid, (4.6 g, 77%); m.p., 83°-84° C.; [α]²⁴ −122.6°, (c 1, CH₃OH). Calculated for C₆₆H₁₁₄N₁₀O₁₃: C, 63.11; H, 9.15; N, 11.05. Found: C, 62.94; H, 9.16; N, 10.88%; δ$_H$ (220 MHz, CDCl₃, 2 Conf.), 0.78-1.03 (39H, m, β-CH₃-(Me)Val and Val, γ-CH₃ of (Me)Leu, CH₃-nLe), 1.23-1.31 (10H, m, CH₃-Ala, D-Ala, β, δ-CH₂-Nle), 1.44 (9H, s, OBuᵗ), 1.53-1.80 (12H, m, β-CH₂, γ-CH of (Me)Leu), 2.04-2.15 (2H, m, β-CH-Val, (Me)Val), 2.71-3.31 (18H, series of s, N-CH₃), 4.28-4.33 (2H, d×d, CH₂-Sar), 4.36 (1H, m, α-CH-Ala), 4.39 (1H, t, α-CH-Nle), 4.65-5.01 (5H, m, α-CH), 5.20 (2H, s, PhCH₂), 5.50-5.52 (2H, m, α-CH-(Me)Leu), 5.92 (1H, br.d., NH-nLe), 6.59 (1H, br.d., NH-Ala), 6.78 (1H, br.d., NH-Val), 6.81-6.95 (1H, br.d., NH-D-Ala) and 7.34 (5H, s, ArH), R$_t$ 11.8 min.; m/z 1225 (M⁺, DCI).

EXAMPLE 9

H-Abu-Sar-(Me)Leu-Val-(Me)Leu-Ala-D-Ala-(Me)-Leu-(Me)Leu-(Me)Val-OBuᵗ

Z-Abu-Sar-(Me)Leu-Val-(Me)Leu-Ala-D-Ala-(Me)-Leu-(Me)Leu-(Me)Val-OBuᵗ (2.45 g, 2 mM; prepared as described in Example 5) in CH₃OH (50 cm³) was hydrogenolysed in the presence of 10% Pd/C catalyst for forty-eight hours. The catalyst was removed by filtration and the filtrate evaporated to give the title compound as a foam. (2.12 g, 97%); m.p., 92°-94° C.; [α]²⁴ −143° (c 1, CH₃OH); m/z 1092 (M+1, FAB).

EXAMPLE 10

H-Thr(Buᵗ)-Sar-(Me)Leu-Val-(Me)Leu-L-Ala-D-Ala-(Me)Leu-(Me)Leu-(Me)Val-OBuᵗ

(10%) Pd/C catalyst (0.21 g) was added to a stirred solution of Z-Thr-(Buᵗ)-Sar-(Me)Leu-Val-(Me)Leu-Ala-D-Ala-(Me)Leu-(Me)Leu-(Me)Val-Obuᵗ(2.1 g, 1.6 mM; pared as described in Example 6) in MeOH (30 cm³) and the mixture hydrogenolysed for forty-six hours. The catalyst was removed by filtration and the filtrate evaporated to dryness to give the title compound (1.7 g, 88%); m.p., 88°-90° C.; [α]²⁰ −68° (c 0.8, CH₃OH). Calculated for C₆₀H₁₁₂N₁₀O₁₂.H₂O: C, 60.90; H, 9.64; N, 11.84. Found: C, 61.16; H, 9.66; N, 11.63%; m/z 1166 (M+1, FAB).

EXAMPLE 11

H-Nva-Sar-(Me)Leu-Val-(Me)Leu-Ala-D-Ala-(Me)-Leu-(Me)Leu-(Me)Val-OBuᵗ

Z-Nva-Sar-(Me)Leu-Val-(Me)Leu-Ala-D-Ala-(Me)-Leu-(Me)Leu-(Me)Val-Obuᵗ (4.96 g, 4 mM; prepared as described in Example 7) in MeOH (50 cm³) was hydrogenolysed at atmospheric pressure in the presence of 10% Pd/C catalyst (0.2 g). The catalyst was removed by filtration and the filtrate evaporated to give the title compound as a white foam, (4.47 g, 94%); [α]²⁴ −170 Å, (c 1, CH₃OH); H δ$_H$ (250 MHz, CDCl₃), 0.74-1.08 (39H, m, γ-CH₃-(Me)Leu, β-CH₃-Val, (Me)Val, CH₃-Nva), 1.23-1.31 (10H, m, CH₃Ala, D-Ala, β, -CH₂-Nva), 1.45 (9H, s, OBuᵗ), 1.53-1.85 (12H, m, β-CH₂, γ-CH-(Me)Leu), 2.20-2.41 12H, m, β-CH-Val, (Me)-Val), 2.79-3.20 (18H, series of s. NCH₃), 4.21 (2H, br.s., —NH₂), 4.34-4.39 (2H, d×d, CH₂-Sar), 4.41-5.52 (9H, m, α-CH), 6.61 (1H, br.d., NH-D-Ala), 6.74 (1H, br.d., NH-Val), and 6.85 (1H, br.d., NH-Ala); m/z 1107 (M+1, FAB).

EXAMPLE 12

H-Nle-Sar-(Me)Leu-Val-(Me)Leu-Ala-D-Ala-(Me)-Leu-(Me)Leu-(Me)Val-OBuᵗ

Z-Nle-Sar-(Me)Leu-Val-(Me)Leu-Ala-D-Ala-(Me)-Leu-(Me)Leu-(Me)Val-OBuᵗ (5.0 g, 4 mM; prepared as described in Example 8) in MeOH (50 cm³) was hydrogenolysed in the presence of 10% Pd/C catalyst (0.2 g) under atmospheric pressure for forty-eight hours. The catalyst was removed by filtration and the filtrate evaporated to give the title compound as a white solid. (4.9 g, 95%); m.p., 84°-86° C.; [α]²³ −162.2°, (c 1.

CH$_3$OH); $\delta_H$ (250 MHz, CDCl$_3$), 0.75-1.08 (39H, m, $\gamma$-$\gamma$-CH$_3$-(Me)Leu, $\beta$-CH$_3$-Val, (Me)Val, CH$_3$-nLe), 1.24-1.31 (12H, m, CH$_3$-Ala, D-Ala, $\beta$, $\delta$-CH$_2$-Nle), 1.45-1.48 (9H, s, OBu$^t$), 1.54-1.85 (12H, $\beta$-CH$_2$, $\gamma$-CH-(Me)Leu), 2.21-2.42 (2H, m, $\beta$-CH-Val, (Me)Val), 2.79-3.20 (18H, series of s, N-CH$_3$), 4.20 (2H, br.s., —NH$_2$), 4.34-4.39 (2H, d$\times$d, $\alpha$-CH-SAR), 4.40-5.52 (9H, m, $\alpha$-CH), 6.61 (1H, br.d., NH-D-Ala), 6.75 (1H, br.d., NH-Val), and 6.83 (1H, br.d., NH-Ala); m/z 1121 (M+1, FAB).

EXAMPLE 13

Z-(Me)Ser(Bu$^t$)-Nle-Sar-(Me)Leu-Val-(Me)Leu-Ala-D-Ala-(Me)Leu-(Me)Leu-(Me)Val-OBu$^t$

To a solution of Z-(Me)Ser(Bu$^t$)-OH (11) (0.46 g, 1.5 mM) in THF (2 cm$^3$) and NMM (0.35 cm$^3$, 1.3 mM) at $-20°$ C. was added a cooled solution of DppCl (0.37 g, 1.5 mM) in THF (5 cm$^3$). The suspension was stirred at $-20°$ C. for ten minutes and then treated with a pre-cooled solution of H-Nle-Sar-(Me)Leu-Valeu-Ala-D-Ala-(Me)Leu-(Me)Leu-(Me)Val-OBu$^t$ (1.44 g, 1.3 mM; prepared as described in Example 12). The reaction mixture was stirred for two hours at $-20°$ C. and thirty-six hours at room temperature and worked-up in the usual way to yield a crude solid. The residue was purified on a silica gel column eluting with EtOAc-DCM (3:1). Evaporation of the appropriate fractions afforded the title compound as a white solid, (1.52 g, 75%); m.p., 72°-73° C.; $[\alpha]^{24} - 145.2°$ (c 1.5, CH$_3$OH). Calculated for C$_{74}$H$_{129}$N$_{11}$O$_{15}$: C, 62.88; H, 9.23; N, 10.90. Found: C, 62.97; H, 9.33; 10.40%; $\delta_H$ (250 MHz, CDCl$_3$, 2 Confs.), 0.73-1.03 (39H, $\beta$-CH$_3$-Val, (Me)Val, $\gamma$-CH$_3$-(Me)Leu, CH$_3$-Nle), 1.12 (9H, s, OBu$^t$-(Me)Ser), 1.22-1.32 (12H, m, CH$_3$Ala, D-Ala, $\beta$, $\delta$, —CH$_2$—Nle), 1.38-1.44 (9H, 2s, OBu$^t$, Conf.), 1.54-1.62 (4H m, $\gamma$-CH-(Me)Leu), 1.63-1.81 (8H, m, $\beta$-CH$_2$-(Me)Leu), 2.04-2.16 (2H, m, $\beta$-CH-Val, (Me)Val), 2.70-3.30 (21H, series of s, NCH$_3$), 3.84 (2H, t, $\beta$-CH$_2$-(Me)Ser), 4.27-4.32 (2H, d$\times$d, $\alpha$-CH$_2$-Sar), 4.35 (1H, m, $\alpha$-CH-Ala), 4.40 (1H, t, $\alpha$-CH-Nle), 4.65 (2H, m, $\alpha$-CH-Val, (Me)Val), 4.69-4.86 (3H, m, $\alpha$-CH-D-Ala, (Me)Leu), 5.13 (2H, s, PhCH$_2$), 5.46 (2H, m, $\alpha$-CH-(Me)Leu), 5.51 (1H, t, $\alpha$-CH-(Me)Ser), 6.89-7.10 (1H, br.d., NH, D-Ala), 7.15-7.20 (1H, br.d., NH-Val), 7.34 (5H, s, ArH), 7.62-7.78 (1H, br.d., NH-Ala), and 7.89-8.07 (1H, br.d., NH-Nle); R$_t$ 15.8 min.; m/z 1412 (M+, DCI).

EXAMPLE 14

Z-(Me)Ser(Bu$^t$)-Nva-Sar-(Me)Leu-Val-(Me)Leu-Ala-D-Ala-(Me)Leu-(Me)Leu-(Me)Val-OBu$^t$

DppCl (0.38 g, 1.5 mM) in THF (5 cm$^3$) was added to a stirred solution of Z-(Me)Ser(Bu$^t$)-OH (11) (0.46 g, 1.5 mM) in THF (2 cm$^3$) and NMM (0.36 cm$^3$, 1.3 mM) at $-20°$ C., and the suspension stirred at this temperature for twenty minutes. A pre-cooled solution of H-Nva-Sar-(Me)Leu-Val-(Me)Leu-Ala-D-Ala-(Me)Leu-(Me)-Leu-(Me)Val-OBu$^t$ (1.43 g, 1.3 mM; prepared as described in Example 11) in THF (5 cm$^3$) was then added to the above mixture and the total mixture stirred at $-20°$ C. for two hours and at ambient temperature for thirty-five hours. The reaction was worked-up as described for the general DppCl procedure and the residue purified on a silica gel column eluting with EtOAc/DCM. Solvent evaporation of the appropriate fractions afforded the title compound as a white foam, (1.41 g, 73%); m.p., 70° C.; $[\alpha]^{25} - 151.4°$ (c 1.4, CH$_3$OH). Calculated for C$_{73}$H$_{127}$N$_{11}$O$_{15}$: C, 62.66; H, 9.15; N, 11.01. Found: C, 62.31; H, 9.26; N, 10.64%; $\delta_H$ (250 MHz, CDCl$_3$, 2 Confs.), 0.72-1.03 (39H, $\gamma$-CH$_3$-(Me)Leu, $\beta$-CH$_3$-Val and (Me)Val, CH$_3$-NVa), 1.13 (9H, s, OBu$^t$, (Me)Ser), 1.21-1.32 (10H, d$\times$d, CH$_3$-Ala, D-Ala, $\beta$, —CH$_2$-Nva), 1.44 (9H, 2s, OBu$^t$, Conf.), 53-1.61 (4H, m, $\gamma$-CH-(Me)Leu), 1.62-1.80 (8H, m, $\beta$-CH$_2$-(Me)Leu), 2.03-3.06 11H, m, $\beta$-CH-Val), 2.11-2.16 (1H, m, $\beta$-CH-(Me)Val), 2.69-3.31 (21H, series of s. N-CH$_3$), 3.83 (2H, t, $\beta$-CH$_2$-(Me)Ser), 4.26-4.31 (2H, d$\times$d, CH$_2$-Sar), 4.34-4.40 (1H, m, $\alpha$-CH-Ala), 4.40 (1H, t, $\alpha$-CH-Nva), 4.64-4.65 (2H, d$\times$d, $\alpha$-CH-(Me)Val, $\alpha$-CH-Val), 4.69-5.08 (3H, m, $\alpha$-CH-(Me)Leu, $\alpha$-CH-D-Ala), 5.12 (2H, s, PhCH$_2$), 5.45 (2H, m, $\alpha$-CH-(Me)Leu), 5.52 (1H, t, $\alpha$-$\overline{\text{CH}}$-(Me)Ser), 6.88-7.09 (1H, br.d., NH-D-Ala), 7.14-7.21 (1H, br.d., NH-Val), 7.33 (5H, s, ArH), 7.61-7.77 (1H, br.d., NH-Ala), and 7.90-8.08 (1H, br.d., NH-Nva); R$_t$ 15.2 min; m/z 1398 (M+, DCI).

EXAMPLE 15

Z-(Me)Ser(Bu$^t$)-Thr(Bu$^t$)-Sar-(Me)Leu-Val-(Me)Leu-Ala-D-Ala-(Me)Leu-(Me)Val-OBu$^t$

N.M.M. (0.4 cm$^3$, 3.6 mM, 2.5 equiv.) was added to a stirred solution of Z-(Me)Ser(Bu$^t$)-OH (11) (0.5 g, 1.6 mM, 1.1 equiv.) in THF (5 cm$^3$) at $-20°$ C. DppCl (0.5 g, 2.2 mM, 1.5 equiv.) in THF (2cm$^3$) was then added and the mixture stirred at $-20°$ C. for twenty minutes, after which time H-Thr(Bu$^t$)-Sar-(Me)Leu-Val-(Me)-Leu-Ala-D-Ala-(Me)Leu-Me)Leu-(Me)Val-OBu$^t$ (1.7 g, 1.4 mM, 1 equiv.; prepared as described in Example 10) in THF (5 cm$^3$) was added. The resulting mixture was stirred at $-20°$ C. for one hour, 0°-5° C. for half an hour and room temperature for four days. The product was worked-up as described in the general DppCl procedure to give an oil, which was purified on a silica gel column eluting with EtOAc. Evaporation of the appropriate fractions afforded the title compound as a white foam (1.1 g, 52%); m.p., 80° C.; $[\alpha]^{20} - 136.4°$ (c 1.0, CH$_3$OH). Calculated for C$_{76}$H$_{133}$N$_{11}$O$_{16}$: C, 62.68 ; H, 9.14; N, 10.58. Found: C, 62.61; H, 9.31; N, 10.19%; $\delta_H$ (250 MHz, CDCl$_3$), 0.98-1.10 (36H, m, CH$_3$ of (Me)Val, (Me)Leu, Val), 1.18 (9H, s, Thr(Bu$^t$), 1.21-1.25 (12H, m, (Me)Ser (Bu$^t$), and Thr-CH$_3$), 1.29-1.31 (6H, d$\times$d, CH$_3$ of L-Ala, D-Ala), 1.54-1.96 (12H, m, $\beta$-CH$_2$ and $\gamma$-CH of (Me)Leu), 2.05-2.32 (2H, m, $\beta$-CH of (Me)-Val, Val), 2.79-3.28 (21H, series of s, N-CH$_3$), 3.22 (1H, d, $\alpha$-CH-Sar), 3.65-3.75 (1H, m, $\beta$-CH of Thr), 4.05-4.10 (2H, m, $\beta$-CH$_2$ of (Me)Ser), 4.25-4.35 (1H, m, $\alpha$-CH-L-Ala), 4.53-4.99 (4H, m. $\alpha$-CH of D-Ala, Val, (Me)Val, Sar), 5.02-5.20 (4H, m, $\alpha$-CH of (Me)Ser, Thr, and Ph-CH$_2$—), 5.48-5.58 (4H, m, $\alpha$-CH of (Me)Leu), 6.92-7.27 (3H, m, N-H), 7.28 (5H, s, Ar-H), and 7.31 (1H, d, NH-L-Ala); m/z 1457 (M+1, FAB); R$_t$ 16 min.

EXAMPLE 16

Z-(Me)Ser(Bu$^t$)-Abu-Sar-(Me)Leu-Val-(Me)Leu-Ala-D-Ala-(Me)Leu-(Me)Leu-(Me)Val-OBu$^t$

N.M.M. (0.9 cm$^3$, 9.7 mM, 2.5 equiv.) was added to a solution of Z-(Me)Ser(Bu$^t$)-OH (1.21 g, 3.9 mM, 1 equiv.) in THF (10 cm$^3$) and the mixture was stirred at $-20°$ C. DppCl (1.38 g. 5.9 mM, 1.5 equiv.) in THF (5 cm$^3$) was then added the resulting mixture stirred at $-20°$ C. for twenty minutes. A pre-cooled solution of H-Abu-Sar-(Me)Leu-Val-(Me)Leu-Ala-D-Ala-(Me)-Leu-(Me)Leu-(Me)Val-OBu$^t$ (3.6 g. 3.3 mM, 1 equiv.; prepared as described in Example 9) in THF 15 cm$^3$) was added and the reaction mixture stirred at $-20°$ C. for one hour. 0°-5° C. for one hour and room temperature for four days. The product was worked-up as described for the general DppCl method, to yield an oil which was purified on a silica gel column eluting with EtOAc/CH$_2$Cl$_2$ (1:3); evaporation of the appropriate fractions gave the title compound as a white solid (1.9 g, 41%); m.p., 80°–81° C.; [α]$^{20}$ –144° (c 1.3, CH$_3$OH). Calculated for C$_{72}$H$_{125}$N$_{11}$O$_{15}$: C, 62.47; H, 9.04; H, 11.14. Found: C, 62.34; H, 9.15; N, 10.94%; δ$_H$ (250 MHz, CDCl$_3$) 0.77–1.02 (39H, m, CH$_3$ of Abu, Val, (Me)Leu, (Me)Val), 1.17 (9H, s, (Me)Ser, (Bu$^t$), 1.24–1.30 (6H, d×d, CH$_3$ of L-Ala, D-Ala), 1.44 (9H, s, (Me)Val-(OBu$^t$), 1.36–2.26 (14H, m, β-CH$_2$ of (Me)Leu and Abu, γ-CH of (Me)Leu), 2.18–2.22 (2H, m, β-CH of Val and (Me)Val), 2.81–3.49 (18H, series of s, N-CH$_3$), 3.12 (1H, d, α-CH-Sar), 3.52–3.77 (2H, m, β-CH$_2$ of (Me)Ser), 3.80 (1H, d, α-CH-Sar), 4.28–4.48 (1H, m, α-CH-L-Ala), 4.67–4.72 (1H, d, α-CH-Val), 4.72–4.76 (1H, d, α-CH-(Me)Val), 4.79–4.96 (2H, m, α-CH, D-Ala and Abu), 5.05–5.15 (5H, m, Ph-CH$_2$— and α-CH of (Me)Leu, (Me)Ser), 5.48–5.52 (1H, m. α-CH-(Me)Leu), 6.90–7.11 (2H, 2s, N-H), 7.27 (5H, s, ArH), 7.85–8.28 (2H, 2s, —NH); m/z 1384 (M+1, FAB); R$_t$ 13.5 min.

EXAMPLE 17

Z-(Me)Thr(Bu$^t$)-Nva-Sar-(Me)Leu-Val-(Me)Leu-Ala-D-Ala-(Me)Leu-(Me)Leu-(Me)Val-OBu$^t$

Z-(Me)Thr-(Bu$^t$)-OH (0.39 g, 1.20 mM) in THF (2 cm$^3$) was activated using DppCl (0.31 g, 1.25 mM) in THF (2 cm$^3$) and NMM (0.3 cm$^3$, 2.5 mM) at –20° C. and coupled to H-Nva-Sar-(Me)Leu-Val-(Me)Leu-Ala-D-Ala-(Me)Leu-(Me)Leu-(Me)Val-OBu$^t$ (1.30 g, 1.17 mM; prepared as described in Example 11) in THF (5 cm$^3$) according to the general DppCl method. The reaction mixture was stirred at –20° C. for two hours and at ambient temperature for forty-five hours, and then worked-up in the usual way. The residue was purified on a silica gel column eluting with EtOAc to give the title compound as a white solid (0.75 g, 65%); m.p., 70°–71° C.; [α]$^{25}$ –175.4°, (c 1, CH$_3$OH). Calculated for C$_{74}$H$_{129}$N$_{11}$O$_{15}$: C, 62.88; H, 9.20; N, 10.90. Found: C, 63.02; H, 9.38; N, 10.70%; δ$_H$ (250 MHz, CDCl$_3$, 2 Confs.), 0.72–1.02 (39H, m, γ-CH$_3$-(Me)Leu, β-CH$_3$-Val, (Me)Val and CH$_3$-Nva), 1.09–1.25 (9H, s, OBu$^t$), 1.09–1.25 (3H, d, β-CH$_3$-(Me)Thr), 1.25–1.35 (12H, m, CH$_3$-Ala, D-Ala, β, δ-CH$^2$-Nva), 1.46–1.48 (9H, 2s, OBu$^t$, Conf.,), 1.52–1.85 (12H, m, β-CH$_2$, γ-CH-(Me)Leu), 2.03–2.16 (2H, β-CH-Val, (Me)Val), 2.70–3.14 (21H, series of s, N-CH$_3$), 4.19 (1H, m, β-CH-(Me)Thr), 4.28–4.36 (2H, d×d), 4.39 (1H, m, α-CH-Ala), 4.44 (1H, t, α-CH-Nva), 4.63–4.70 (2H, m, α-CH-Val, (Me)Val), 4.67–5.08 (3H, m, α-CH-D-Ala, (Me)Leu), 5.12 (2H, s, PhCH$_2$), 5.45 (2H, m, α-CH-(Me)Leu), 6.88–7.09 (1H, br.d., NH-D-Ala), 7.13–7.18 (1H, br.d., NH-Val), 7.33 (5H, s, ArH) 7.61–7.78 (1H br.d., NH-Ala) and 7.88–8.05 (1H br.d., NH-Nva): R$_t$ 14.8 min.; m/z 1411 (M+, DCI).

EXAMPLE 18

Z-(Me)Thr(Bu$^t$)-Nle-Sar-(Me)Leu-Val-(Me)Leu-Ala-D-Ala-(Me)Leu-(Me)Leu-(Me)Val-OBu$^t$

Z-(Me)Thr(Bu$^t$)-OH (0.40 g, 1.25 mM) in THF (2 cm$^3$) was activated using DppCl (0.31 g, 1.24 mM) in THF (2 cm$^3$) and NMM (0.3 cm$^3$, 2.50 mM) at –20° C., and coupled to N-Nle-Sar-(Me)Leu-Val-(Me)Leu- Ala-D-Ala-(Me)Leu-(Me)Leu-(Me)Val-OBu$^t$ (1.38 g, 1.24 mM; prepared as described in Example 12) in THF (2 cm$^3$), according to the general DppCl method. The reaction mixture was stirred at –20° C. for two hours and ambient temperature for forty-five hours, and then worked-up as described for the general DppCl method. The residue was purified on a silica gel column eluting with EtOAc/DCM (1:1), to give the title compound as a white foam (0.71 g, 64%); [α]$^{24}$ –150.4° (c 1.2, CH$_3$OH). Calculated for C$_{75}$H$_{131}$N$_{11}$O$_{15}$: C, 63.11; H, 9.26; N, 10.80. Found: C, 63.00; H, 9.52; N, 11.03%; δ$_H$ (250 MHz, CDCl$_3$, 2 Confs.), 0.73–1.02 (39H, m, γ-CH$_3$-(Me)Leu, β-CH$_3$-(Me)Val, Val and CH$_3$-Nle), 1.08–1.25 (12H, m, β-CH$_3$-(Me)Thr, OBu$^t$-(Me)Thr), 1.25–1.35 (12H, m, CH$_3$-Ala, D-Ala, CH$_2$-Nle), 1.46–1.49 (9H, 2s, OBu$^t$, Conf.), 1.52 1.85 (12H, m, β-CH$_2$ and γ-CH-(Me)Leu), 2.04–2.16 (2H, m, β-CH-Val, (Me)Val), 2.70–3.14 (21H, series of s, N-CH$_3$), 4.19 (1H, m, β-CH-(Me)Thr), 4.29–4.37 (2H, d×d, CH$_2$-Sar), 4.39 (1H, m, α-CH-Ala), 4.44 (1H, t, α-CH-Nle), 4.64 (3H, m, α-CH), 4.68–5.07 (3H, m, α-CH-D-Ala, (Me)Leu), 5.12 (2H, s, PhCH$_2$), 5.46 (2H, m, α-CH-(Me)Leu), 6.8–7.09 (1H, br.d., NH-D-Ala), 7.14–7.19 (1H, br.d., NH-Val), 7.33 (5H, s, ArH), 7.62–7.79 (1H, br.d., NH-Ala), and 7.89–8.06 (1H, br.d., NH-Nle); R$_t$ 15.7 min; m/z 1425 (M+, DCI).

EXAMPLE 19

Z-(Me)Thr(Bu$^t$)-Abu-Sar-(Me)Leu-Val-(Me)Leu-Ala-D-Ala-(Me)Leu-(Me)Leu-(Me)Val-OBu$^t$

N.M.M. (1.0 cm$^3$, 6.5 mM, 2.5 equiv.) was added to a solution of Z-(Me)Thr(Bu$^t$)-OH (1 g, 3.1 mM, 1.2 equiv.) in THF (10 cm$^3$), and the mixture stirred at –20° C. DppCl (0.9 g, 3.9 mmol, 1.5 equiv.) in THF (5 cm$^3$) was then added, and the resulting mixture stirred at –20° C. for twenty minutes. A pre-cooled solution of H-Abu-Sar-(Me)Leu-Val-(Me)Leu-Ala-D-Ala-(Me)-Leu-(Me)Leu-(Me)Val-OBu$^t$ (2.8 g, 2.6 mM, 1 equiv.; prepared as described in Example 9) in THF (10 cm$^3$) was added and the reaction mixture was stirred at –20° C. for one hour, 0° C. for one hour and room temperature for two days. The product was worked up as described for the general DppCl procedure, to yield an oil which was purified on a silica gel column eluting with EtOAc. Evaporation of the appropriate fractions gave the title compound as a white foam, (3.1 g, 86%); m.p., 92°–93° C.; [α]$^{20}$ –164 (c 1.0, MeOH). Calculated for C$_{73}$H$_{126}$N$_{11}$O$_{15}$: C, 62.66; H, 9.01; N, 11.02. Found: C, 62.60; H, 9.07; N, 11.03%; δ$_H$ (250 MHz, CDCl$_3$), 0.77 1.12 (39H, m, CH$_3$ of Abu, Val (Me)Leu, (Me)Val), 1.13–1.19 (3H d, γ-CH$_3$-(Me)Thr), 1.20 (9H, s, (Me)Thr(Bu$^t$), 1.29–1.32 (6H, d×d, CH$_3$ of L-Ala and D-Ala), 1.44 (9H, s, (Me)Val(OBu$^t$), 1.52–1.89 (10H, m, β-CH$_2$ of Abu, (Me)Leu), 1.84–2.22 (6H, m, β-CH of Val and (Me)Val and γ-CH (Me)Leu), 2.72–3.34 (21H, series of s, N-CH$_3$), 3.21 (1H, d, α-CH-Sar), 4.19–4.32 (1H, qt, β-CH-(Me)Thr), 4.33–4.41 (1H, m, α-CH-Ala), 4.50–4.90 (4H, m, α-CH of Sar, (Me)Val, D-Ala and Val), 4.94–5.09 (3H, m, α-CH-Abu, α-CH(Me)Leu), 5.12 (2H, s, Ph-CH$_2$), 5.15 (1H, d, α-CH(Me)Thr), 5.49–5.69 (2H, m, α-CH-(Me)Leu), 6.80–6.93 (2H, 2s, N-H), 7.35 (5H, s. ArH), 7.67–7.99 (2H, 2s, —NH); m/z 1398 (M+, CI); R$_t$ 12.2 min.

EXAMPLE 20

Fmoc-(Me)Thr(Bu$^t$)-Abu-Sar-(Me)Leu-Val-(Me)Leu-Ala-D-Ala-(Me)Leu-(Me)Leu-(Me)Val-OBu$^t$ Triethylamine (0.25 cm$^3$, 1.78 mM, 1.5 equiv.) was added to a stirred solution of Fmoc(Me)Thr(Bu$^t$-OH (16) (0.73 g, 1.78 mM, 1.5 equiv.) in THF (15 cm$^3$) at –20° C. DppCl (0.42 g, 1.78 mM, 1.5 equiv.) in THF (2 cm³) was then added and the mixture stirred at −20° C. for twenty minutes, after which time H-Abu-Sar-(Me)-Leu-Val-(Me)Leu-Ala-D-Ala-(Me)Leu-(Me)Leu-(Me)-Val-OBu$^t$ (1.27 g, 1.16 mM, 1 equiv.; prepared as described in Example 9) in THF (5 cm³) was added. The resulting mixture was stirred at −20° C. for one hour, 0°-5° C. for half an hour and room temperature for four days. The product was worked-up as described in the general DppCl procedure to give an oil which was purified on a silica gel column eluting with CH$_2$Cl$_2$/MeOH 12:1. Evaporation of the appropriate fractions gave the title compound as a white foam (1.11 g, 69%); m.p., 94°-96° C.; [α]$^{20}$ −121° (c 1.0. CH$_3$OH); δ$_H$ (CDCl$_3$, 220 MHz). Calculated for C$_{80}$H$_{131}$N$_{11}$O$_{15}$: C, 64.65; H, 8.82; N, 10.37. Found: C, 64.51; H, 8.93; N, 10.43%; δH (CDCl$_3$, 250 MHz), 0.77-1.10 (39H, m, CH$_3$ of Abu, Val, (Me)Val, (Me)Leu)), 1.11-1.28 (12H, m, CH$_3$(Me)Thr, (Me)Thr(Bu$^t$), 1.29-1.30 (6H, d×d, CH$_3$-Ala, D-Ala), 1.44 (9H, s, (Me)Val-OBu$^t$), 1.53-1.72 (10H, m, β-CH$_2$ of (Me)Leu-Abu), 1.73-2.20 (6H, m, β-CH, Val, (Me)Val), 2.79-3.21 (21H, series of s, N-CH$_3$), 3.22 (1H, d, α-CH-Sar), 3.92 (1H, m, β-CH, (Me)Thr), 4.12-5.02 (9H, m, α-CH), 5.12 (2H, s, Fmoc-CH$_2$), 5.34-5.62 (2H, m, α-CH), 6.61-6.92 (2H, m, N—H), and 7.23-7.80 (9H, m, ArH, N—H); m/z 1486 (M+1, FAB); R$_t$ 15.2 (λ 280 nm).

EXAMPLE 21

Boc-Dab(Fmoc)-Abu-Sar-(Me)Leu-Val-(Me)Leu-Ala-D-Ala-(Me)Leu-(Me)Leu-(Me)Val-OBu$^t$ N.M.M. (0.5 cm³, 4.4 mM, 2.5 equiv.) was added to a solution of Boc-Dab(Fmoc)-OH (18) (0.8 g, 1.9 mM, 1.1 equiv.) in THF (5 cm³), and the mixture stirred at −20° C. DppCl (0.6 g, 2.1 mM, 1.5 equiv.) in THF (3 cm³) was then added and the resulting mixture stirred at −20° C. for twenty minutes. A pre-cooled solution of H-Abu-Sar-(Me)Leu-Val-(Me)Leu-Ala-D-Ala-(Me)-Leu-(Me)Leu-(Me)Val-OBu$^t$ (1.9 g, 1.7 mM, 1 equiv.; prepared as described in Example 9) in THF (10 cm³) was added and the reaction mixture stirred at −20° C. for one hour, 0° C. for one hour and room temperature for three days. The solvent was evaporated and the residue worked-up as described in the usual way. Purification of the product on a silica column eluting with MeOH/EtOAc 1:5 afforded the title compound as a white foam (2.1 g, 81%); m.p., 109°-110° C.; [α]$^{20}$ −130.7° (c 0.8, MeOH). Calculated for C$_{80}$H$_{130}$N$_{12}$O$_{16}$/H$_2$O: C, 62.66; H, 8.62; N, 10.97. Found: C, 62.90; H, 8.75; N, 10.92%; δ$_H$ (250 MHz, CDCl$_3$), 0.79-1.05 (39H, m, CH$_3$ of Val, (Me)Val, (Me)-Leu, Abu), 1.27-1.29 (6H, m, CH$_3$ of L-Ala, D-Ala), 1.46 (9H, s, (Me)Val(OBu$^t$), 1.47-2.15 (16H, m, β-CH$_2$ of (Me)Leu, Abu, Dab, γ-CH of (Me)Leu), 2.17-2.23 (12H, m, β-CH of Val, (Me)Val), 2.77-3.28 (18H, series of s, N-CH$_3$), 4.19-4.48 (4H, m, γ-CH$_2$ of Dab, α-CH of Sar, α-CH of L-Ala), 4.71-4.90 (5H, m, α-CH of Sar, Val, D-Ala, Abu), 5.01 (2H, s, Fmoc-CH$_2$—), 5.02-5.27 (5H, m, α-CH of Dab, (Me)Leu), 5.47-5.49 (1H, m, Dab-NH), 6.01 (1H, d, Dab-NH), 6.90-7.21 (2H, 2s, —NH), 7.25-7.28 (8H, m, ArH), and 7.31-8.10 (2H, 2s, -NH); m/z 1514 (M+1, FAB); R$_t$ 11.7 min.

EXAMPLE 22

Z-Hyp(Bu$^t$)-Abu-Sar-(Me)Leu-Val-(Me)Leu-Ala-D-Ala-(Me)Leu-(Me)Leu-(Me)Val-OBu$^t$

N.M.M. (1.3 cm³, 12.3 mM, 2.5 equiv.) was added to a solution of Z-Hyp(Bu$^t$)-OH (21) (1.7 g, 5.3 mM, 1 equiv.) in THF (10 cm³) and the mixture stirred at −20° C. DppCl (1.7 g, 7.4 mM, 1.5 equiv.) in THF (5 cm³) was then added and the resulting mixture stirred at −20° C. for twenty minutes. A pre-cooled solution of H-Abu-Sar-(Me)Leu-Val-(Me)Leu-Ala-D-Ala-(Me)-Leu-(Me)Leu-(Me)Val-OBu$^t$ (5.1 g, 4.9 mM, 1 equiv.; prepared as described in Example 9) in THF (5 cm³) was added and the reaction mixtured stirred at −20° C. for one hour, 0°-15° C. for one hour and room temperature for two days. The product was worked-up as described for the general DppCl method to yield a yellow oil, which was purified on a silica gel column eluting with CH$_2$Cl$_2$/EtOAc (3:1). Evaporation of the appropriate fractions afforded the title compound as a white foam (6 g, 92%); m.p., 94°-95° C.; [α]$^{20}$ −128° (c 1.0, CH$_3$OH). Calculated for C$_{73}$H$_{125}$N$_{11}$O$_{15}$: C, 62.80; H, 8.96; N, 11.04. Found: C, 62.41; H, 9.02; N, 10.69%; δ$_H$ (250 MHz, CDCl$_3$), 0.74-1.03 (39H, m, CH$_3$ of Abu, Val, (Me)Leu, (Me)Val), 1.17 (9H, 2s, Hyp (Bu$^t$), 1.27-1.34 (6H, d×d, CH$_3$ D-Ala, L-Ala), 1.45 (9H, s, (Me)Val-OBu$^t$), 1.46-2.01 (10H, m, β-CH$_2$ of Abu, (Me)Leu), 2.02-2.36 (8H, m, β-CH of Val. (Me)Val, Hyp and γ-CH of (Me)Leu), 2.93-3.30 (21H, series of s, N-CH$_3$), 3.11-3.12 (1H, m, α-CH-Sar), 3.23-3.80 (2H, d×d, δ-CH$_2$ of Hyp), 3.99-4.25 (1H γ-CH of Hyp) 4.32-4.43 (1H α-CH of L-Ala), 4.49-4.94 (5H, m, α-CH of Val, (Me)Val, Sar, Abu and D-Ala) 5.13 (2H s, Ph-CH$_2$), 5.14-5.31 (4H, m, α-CH-(Me)Leu), 5.48-5.52 (1H, m. α-CH of Hyp), 7.14-7.30 (2H, 2s, NH of D-Ala, Val), 7.34 (1H, s, NH-L-Ala), 7.35 (5H, s, ArH), and 8.10 (1H, s, NH-Abu); m/z 1396 (M+1, FAB); R$_t$ 11.4 min.

EXAMPLE 23

Z-Hyp(Bu$^t$)-Nle-Sar-(Me)Leu-Val-(Me)Leu-Ala-D-Ala-(Me)Leu-(Me)Leu-(Me)Val-OBu$^t$

Z-Hyp(Bu$^t$)-OH (21) (1.29 g, 4 mM) in THF (5 cm³), NMM (1.2 cm³, 10.8 mM) in THF (5 cm³) were treated with DppCl (1.73 g, 7.3 mM) in THF (5 cm³) at −20° C., and coupled to H-Nle-Sar-(Me)Leu-Val-(Me)Leu-Ala-D-Ala-(Me)Leu-(Me)Leu-Me)Leu-(Me)Val-Obu$^t$ (4.1 g, 3.7 mM; prepared as described in Example 12) in THF (15 cm³) according to the general procedure. The reaction mixture was stirred for two hours at −20° C. and forty-five hours at room temperature. The reaction was worked-up in the usual way and the residue obtained was purified on a silica gel column eluting with EtOAc/DCM. (2:1). Evaporation of the appropriate fractions gave the title compound as a white foam, (4.1 g, 68%); m.p., 95° C.; [α]$^{24}$ −140.4° (c 1.1, CH$_3$OH). Calculated for C$_{75}$H$_{130}$N$_{11}$O$_{15}$: C, 63.15; H, 9.19; N, 10.80. Found: C, 63.02; H, 9.05; N, 11.09%; δ$_H$ (250 MHz, CDCl$_3$2 Conf.), 0.77-1.03 (39H, m, β-CH$_3$-Val, (Me)Val, CH$_3$Nle, CH$_3$-(Me)Leu), 1.14-1.17 (9H, 2s, Hyp(Bu$^t$), Conf.), 1.21-1.35 (16H, d×d, CH$_3$-Ala, D-Ala), 1.21-1.35 (6H, m, β and δ CH$_2$Nle), 1.44-1.46 (9H, 2s, OBu$^t$, Conf.) 1.61-1.68 (8H, m, β-CH$_2$-(Me)Leu), 2.01-2.09 (1H, m, β-CH-Val), 2.13-2.25 (2H, m, β-CH-(Me)Val, β-CH-Hyp), 2.93-3.30 (18H, series of s, N-CH$_3$), 3.23-3.80 (2H, d×d, δ-CH$_2$-Hyp), 3.99-4.25 (1H, m, γ-CH-Hyp), 4.24-4.34 (2H, d×d, CH$_2$-Sar), 4.37 (1H, m, α-CH-Ala), 4.44 (1H, t, α-CN-Nle), 4.50-4.65 (3H, m, α-CH-(Me)Val, Val, Hyp), 4.72-4.76 (2H, m, α-CH-(Me)Leu), 5.12-5.15 (1H, t, α-CH-D-Ala), 5.13 (2H, s, PhCH$_2$), 5.43-5.52 (2H, m, α-CH-(Me)Leu), 6.90-7.19 (2H, br.d., NH-Val, NH-D-Ala), 7.34 (5H, s, ArH), 7.64 (1H, br.d., NH-Ala), and 7.88–8.07 (1H, br.d., NH-Nle); $R_t$ 11.8 min.; m/z 1424 (M+, DCI).

EXAMPLE 24

Z-(Me)Ser-Abu-Sar-(Me)Leu-Val-(Me)Leu-Ala-D-Ala-(Me)Leu-(Me)Leu-(Me)Val-OH

90% TFA (5 cm$^3$) was added to Z-(Me)Ser-Abu-Sar-(Me)Leu-Val-(Me)Leu-Ala-D-Ala-(Me)Leu-(Me)Leu-(Me)Val-OBu$^t$ (1.8 g, 1.3 mM; prepared as described in Example 16) and stirred at room temperature for four hours. The residue (after evaporating TFA under vacuo) was applied directly on a silica gel column eluting with CH$_2$Cl$_2$/MeOH (12:1). Evaporation of the appropriate fractions gave the title compound as a white solid (1.3 g, 79%); m.p., 112°–114° C.; $[\alpha]^{20}$ −127° (c 0.9, CH$_3$OH). Calculated for C$_{64}$H$_{109}$N$_{11}$O$_{15}$.H$_2$O: C, 57.96; H, 8.68; N, 11.62. Found: C, 57.63; H, 8.31; N, 11.20%; m/z 1272 (M+, DCI); $R_t$ 17.0 min.

EXAMPLE 25

H-(Me)Ser-Abu-Sar-(Me)Leu-Val-(Me)Leu-Ala-D-Ala-(Me)Leu-(Me)Leu-(Me)Val-OH

10% Pd/C catalyst (0.12 g) was added to a stirred solution of Z-(Me)Ser-Abu-Sar-(Me)Leu-Val-(Me)Leu-Ala-D-Ala-(Me)Leu-(Me)Leu-(Me)Val-OH (1.2 g, 0.9 mM; prepared as described in Example 24) in CH$_3$OH (30 cm$^3$) and the mixture hydrogenolysed for twenty-four hours. The catalyst was removed by filtration and the filtrate evaporated to give the title compound (1.03 g, 96%); m.p., 135°–137° C.; $[\alpha]^{20}$ −142° (c 1.1, CH$_3$OH). Calculated for C$_{56}$H$_{103}$N$_{11}$O$_{13}$; C, 59.10; H, 9.76; N, 13.54. Found: C, 59.25; H, 9.67; N, 13.40%; m/z 1138 (M+, DCI).

EXAMPLE 26

Z-Hyp-Abu-Sar-(Me)Leu-Val-(Me)Leu-Ala-D-Ala-(Me)Leu-(Me)Leu-(Me)Val-OH

90% TFA (10 cm$^3$) was added to Z-Hyp(Bu$^t$)-Abu-Sar-(Me)Leu-Val-(Me)Leu-Ala-D-Ala-(Me)Leu-(Me)Leu-(Me)Val-OBu$^t$ (4.3 g, 3.1 mM; prepared as described in Example 22) and the mixture stirred at room temperature for four hours. TFA was removed under vacuo and the residue purified on a silica gel column eluting with CH$_2$Cl$_2$:MeOH (15:1). Evaporation of the appropriate fractions gave the title compound as a white solid (2.6g, 65%); m.p., 124°–125° C.; $[\alpha]^{20}$ −143.5° (c 0.6, CH$_3$OH). Calculated for C$_{65}$H$_{109}$N$_{11}$O$_{15}$.2H$_2$O: C, 59.14: H, 8.57; N, 11.68. Found: C, 59.18 ; H, 8.34; N, 11.16%; m/z 1283 (M+, CI); $R_t$ 9.2 min.

EXAMPLE 27

H-Hyp-Abu-Sar-(Me)Leu-Val-(Me)Leu-Ala-D-Ala-(Me)Leu-(Me)Leu-(Me)Val-OH

10% Pd/C catalyst was added to a stirred solution of Z-Hyp-Abu-Sar-(Me)Leu-Val-(Me)Leu-Ala-D-Ala-(Me)Leu-(Me)Leu-(Me)Val-OH (2.6 g, 2 mM; prepared as described in Example 26) and the mixture hydrogenolysed for twenty-three hours. The catalyst was removed by filtration and the filtrate evaporated to dryness to afford the title compound (2.2 g, 96%); m.p., 140°–141° C.; $[\alpha]^{20}$ −161.9° (c 1.0, CH$_3$OH); m/z 1149 (M+, EI).

EXAMPLE 28

H-Dab(Fmoc)-Abu-Sar-(Me)Leu-Val-(Me)Leu-Ala-D-Ala-(Me)Leu-(Me)Leu-(Me)Val-OH.TFA 90% TFA (4 cm$^3$) was added to Boc-Dab(Fmoc)-Abu-Sar-(Me)Leu-Val-(Me)Leu-Ala-D-Ala-(Me)Leu-(Me)Leu-(Me)Val-OBu$^t$ (1 g, 0.7 mM; prepared as described in Example 21) with stirring at −20° C. The mixture was allowed to warm to room temperature with stirring for three and a half hours. TFA was evaporated and the residue triturated with ether, to give the title compound as a white solid (0.9 g, 100%); m.p., 119°–120° C.; $[\alpha]^{20}$ −101.8° (c 0.8, CH$_3$OH); m/z 1350 (M+1, FAB); $R_t$ 20.5 min.; ($\gamma$ 278 nm).

EXAMPLE 29

Z-(Me)Ser-Nva-Sar-(Me)Leu-Val-(Me)Leu-Ala-D-Ala-(Me)Leu-(Me)Leu-(Me)Val-OH

Z-(Me)Ser-Nva-Sar-(Me)Leu-Val-(Me)Leu-Ala-D-Ala-(Me)Leu-(Me)Leu-(Me)Val-Obu$^t$ (1.2 g, 0.9 mM; prepared as described in Example 14) was treated with 90% TFA (6 cm$^3$) at ambient temperature for two hours and at 0° C. overnight. Removal of excess TFA, followed by silica gel chromatography using CH$_2$Cl$_2$/6% MeOH as eluants gave the title compound as a white solid (0.9 g, 60%); m.p., 110°–112° C.; $[\alpha]^{24}$ −134.9° (c 1.02, CH$_3$OH); $R_t$ 10.6 min.; m/z 1286 (M+, EI).

EXAMPLE 50

H-(Me)Ser-Nva-Sar-(Me)Leu-Val-(Me)Leu-Ala-D-Ala-(Me)Leu-(Me)Leu-(Me)Val-OH

Z-(Me)Ser-Nva-Sar-(Me)Leu-Val-(Me)Leu-Ala-D-Ala-(Me)Leu-(Me)Leu-(Me)Val-OH (0.8 g, 0.6 mM; prepared as described in Example 29) in CH$_3$OH (50 cm$^3$) was hydrogenolysed in the presence of 10% Pd/C for forty-eight hour at ambient temperature under one atmosphere of pressure. The catalyst was removed by filtration and the solvent was evaporated to give a solid, which was purified on a Sephadex G10 column eluting with water. Evaporation of the appropriate fractions afforded a solid which was crystallised from methanol/ether to give the title compound as a white solid (0.65 g, 83%); m.p., 192°–194° C.; $[\alpha]^{24}$ −101.6°; m/z 1153 (M+1, FAB).

EXAMPLE 31

Z-(Me)Thr-Nle-Sar-(Me)Leu-Val-(Me)Leu-Ala-D-Ala-(Me)Leu-(Me)Leu-(Me)Val-OH

Z-(Me)Thr-Nle-Sar-(Me)Leu-Val-(Me)Leu-Ala-D-Ala-(Me)Leu-(Me)Leu-(Me)Val-OBu$^t$ (0.53 g, 0.40 mM; prepared as described in Example 18) was treated with 90% TFA (5 cm$^3$) at room temperature for two hours and overnight at 0° C. Excess TFA was removed under vacuo and the residue chromatographed on SEPHADEX LH20 column eluting with DMF. Evaporation of the appropriate fractions afforded the title compound as a white solid (0.31 g, 60%); m.p., 103°–105° C.; $[\alpha]^{25}$ −108.8° (c 1.1, CH$_3$OH), δH (250 MHz, CDCl$_3$), 0.70–1.03 (39H, m, β-CH$_3$-(Me) Val, Val, γ-CH$_3$-(Me)-Leu, CH$_3$-nLe), 1.12 (3H, d, CH$_3$—(Me)Thr), 1.13–1.26 (6H, d×d, CH$_3$-Ala, D-Ala), 1.26–1.29 (6H, m, CH$_2$-Nle), 1.36–1.91 (12H, m, β-CH$_2$, γ-CH-(Me)Leu), 1.92–2.02 (2H, m, β-CH-Val, (Me)Val), 2.75–3.25 (21H, series of s, N-CH$_3$), 4.18 (1H, m, β-CH-(Me)Thr). 4.28–4.38 (2H, br.d., CH$_2$-Sar), 4.38–5.16 (8H, m, α-CH), 5.15 (2H, s, CH$_2$-pH), 5.20–5.53 (2H, m, α-CH)

6.38-7.14 (1H, m, NH-D-Ala), 7.15-7.21 (1H, br.m., NH-Val), 7.35 (5H, s, ArH), 7.60-7.76 (1H, br.d., NH-Ala), and 7.89-8.06 (1H, br.d., NH-Nle); m/z 1314 (M+1, FAB).

EXAMPLE 32

H-(Me)Thr-Nle-Sar-(Me)Leu-Val-(Me)Leu-Ala-D-Ala-(Me)Leu-(Me)Leu-(Me)Val-OH

Z-(Me)Thr-Nle-Sar-(Me)Leu-Val-(Me)Leu-Ala-D-Ala-(Me)Leu-(Me)Leu-(Me)Val-OH (0.28 g, 0.18 mM; prepared as described in Example 31) in CH$_3$OH (20 cm$^3$) was hydrogenolysed in the presence of 10% Pd/C (50 mg) for forty-eight hours at one atmosphere of pressure. The solution, after removal of the catalyst by filtration, was evaporated to dryness and the residue chromatographed on a Sephadex G10 column, eluting with water. Evaporation of the appropriate fractions afforded the title compound which was recrystallised from methanol/ether (0.220 g, 89%); m.p , 120°-122° C.; $[\alpha]^{24} -161.6°$ (c 1.2, CH$_3$OH); m/z 1181 (M+1, FAB).

EXAMPLE 33

Z-(Me)Ser-Nle-Sar-(Me)Leu-Val-(Me)Leu-Ala-D-Ala-(Me)Leu-(Me)Leu-(Me)Val-OH

Z-(Me)Ser-Nle-Sar-(Me)Leu-Val-(Me)Leu-Ala-D-Ala-(Me)Leu-(Me)Leu-(Me)Val-OBu$^t$ (1.41 g, 1 mM; prepared as described in Example 13) was treated with 90% TFA (5 cm$^3$) at ambient temperature for two hours and at 0° C. overnight. Excess TFA was evaporated (under vacuo) and the residue purified on a silica gel column eluting with CHCl$_3$/5% MeOH. Evaporation of the appropriate fractions gave the title compound as a white foam, (0.91 g, 75%); $[\alpha]^{24} -106.3°$ (c 1.2, CH$_3$OH); m/z 1314; (M+, DCI) ; R$_t$ 11.4 min.

EXAMPLE 34

H-(Me)Ser-Nle-Sar-(Me)Leu-Val-(Me)Leu-Ala-D-Ala-(Me)Leu-(Me)Leu-(Me)Val-OH

Z-(Me)Ser-Nle-Sar-(Me)Leu-Val-(Me)Leu-Ala-D-Ala-(Me)Leu-(Me)Leu-(Me)Val-OH (0.9 g, 0.73 mM; prepared as described in Example 33) in CH$_3$OH (50 cm$^3$) was hydrogenolysed in the presence of 10% Pd/C (0.1 g) for forty hours at one atmosphere of pressure. The catalyst was removed by filtration and the solvent evaporated to give a solid, which was chromatographed on a Sephadex G10 column eluting with water. The residue obtained was solidified by trituration with ether and the triturated with ether/petroleum ether, to give the title compound as a white solid (0.75 g, 81%); m.p., 78°-79° C.; $[\alpha]^{24} -136.1°$ (c1.0, CH$_3$OH); m/z (1167) (M+1, FAB).

EXAMPLE 35

Z-Hyp-Nle-Sar-(Me)Leu-Val-(Me)Leu-Ala-D-Ala-(Me)Leu-(Me)Leu-(Me) Val-OH

Z-Hyp(Bu$^t$)-Nle-Sar-(Me)Leu-Val-(Me) Leu-Ala-D-Ala-(Me)Leu-(Me)Leu-(Me)Val-OBu$^t$ (2.8 g, 1.97 mM; prepared as described in Example 23) was treated with 90% TFA (5 cm$^3$) at ambient temperature for one hour and -5° C. overnight. Excess TFA was removed under vacuo and the residue chromatographed on a silica gel column eluting with CHCl$_3$/5% MeOH. Evaporation of the appropriate fractions gave the title compound as a white solid (2.0 g, 77%); m.p., 120°-122° C.; $[\alpha]^{24} -141.8°$ (c 1.0, CH$_3$OH); δH (250 MHz, CDCl$_3$), 0.72-1.06 (39H, m, γ-CH$_3$-(Me)Leu, β-CH$_3$-(Me)Val, CH$_3$-Nle), 1.15-1.25 (6H, d×d, CH$_3$Ala, D-Ala), 1.28 (6H, m, CH$_2$-Nle), 1.36-1.80 (m, β-CH$_2$, γ-CH-(Me)Leu), 1.85-2.26 (m, β-CH-(Me)Val, Val, Hyp), 2.78-3.29 (18H, series of s, N-CH$_3$), 3.23-4.25 (3H, m, γ-CH, δCH$_2$-Hyp), 4.32 (2H, d, CH$_2$-Sar), 4.37-5.1 (8H, m, α-CH), 5.11 (2H, s, Ph-CH$_2$), 5.43-5.52 (2H, m, α-CH), 6.40 (1H, br.s., NH-D-Ala), 7.28 (5H, s, ArH), 8.07-8.39 (3H, br.m., —NH); R$_t$ 11.4 min.; m/z 1312 (M+1, FAB).

EXAMPLE 36

H-Hyp-Nle-Sar-(Me)Leu-Val-(Me)Leu-Ala-D-Ala-(Me)Leu-(Me)Leu-(Me)Val-OH

Z-Hyp-Nle-Sar-(Me)Leu-Val-(Me)Leu-Ala-D-Ala-(Me)Leu-(Me)Leu-(Me)Val-OH (2.62 g, 2 mM; prepared as described in Example 35) in CH$_3$OH (50 cm$^3$) was hydrogenolysed in the presence of 10% Pd/C catalyst (0.15 g) for forty-eight hours. The catalyst was removed by filtration and the filtrate evaporated to give a solid, which was chromatographed on a SEPHADEX G10 column eluting with water. Evaporation of the appropriate fractions gave the title compound as a white solid (1.8 g, 79%); m.p., 139°-141° C.; $[\alpha]^{23} -127.8°$ (c 1.2, CH$_3$OH); m/z 1178 (M+1, FAB).

EXAMPLE 37

Z-(Me)Ser-Thr-Sar-(Me)Leu-Val-(Me)Leu-Ala-D-Ala-(Me)Leu-(Me)Leu-(Me)Val-OH

90% TFA (5 cm$^3$) was added to Z-(Me)Ser(Bu$^t$)-Thr(Bu$^t$)-Sar-(Me)Leu-Val-(Me)Leu-Ala-D-Ala-(Me)-Leu-(Me)Leu-(Me)Val-OBu$^t$ (0.9 g, 0.6 mM; prepared as described in Example 15) and the mixture stirred at room temperature for four hours. The residue, after evaporating TFA was applied directly on a silica gel column eluting with CH$_2$Cl$_2$:MeOH (12:1). Evaporate of the appropriate fractions gave the title compound as a white solid (0.4 g, 50%); m.p., 119°-120° C.; $[\alpha]^{20} -146.6°$ (c 1.1, CH$_3$OH). C$_{69}$H$_{109}$N$_{11}$O$_{16}$1.H$_2$O: C, 58.14; H, 8.41; N, 11.66. Found: C, 57.90; H, 8.33; N, 11.35%; m.z 1287 (M+, DCI); R$_t$ 8.1 min.

EXAMPLE 38

H-(Me)Ser-Thr-Sar-(Me) Leu-Val-(Me)Leu-Ala-D-Ala-(Me)Leu-(Me)Leu-(Me)-Val-OH

10% Pd/C catalyst (0.3 g) was added to a solution of Z-(Me)Ser)-Thr-Sar-(Me)Leu)-Val-(Me)Leu-Ala-D-Ala-(Me)Leu-(Me)Leu-(Me)Val-OH (300 mg, 0.23 mM; prepared as described in Example 37) in CH$_3$OH (20 cm$^3$) and the mixture hydrogenolysed for forty-six hours. The catalyst was removed by filtration and the filtrate evaporated to dryness to give the title compound as a white solid (0.23 g, 95%); m.p., 140°-141° C.; $[\alpha]^{20} -141°$ (c 0.9, CH$_3$OH); m/z 1153 (M+, DCI).

EXAMPLE 39

Cyclo-[(Me)Ser-Abu-Sar-(Me)Leu-Val-(Me)Leu-Ala-D-Ala-(Me)Leu-(Me)Leu-(Me)Val]

DMAP (0.27 2.2 mM, 4 equiv.), followed by the Castro reagent BOP (0.78 g, 1.76 mM, 4 equiv.) were added to a vigorously stirred solution of H-(Me)Ser-Abu-Sar-(Me)Leu-Val-(Me) Leu-Ala-D-Ala-(Me)Leu-(Me)Leu-(Me)Val-OH (0.5 g, 0.44 mM, 1 equiv.; prepared as described in Example 25) in CH$_2$Cl$_2$) (2.51) at room temperature. After three days the solvent was evaporated and the residue applied directly on a silica gel column eluting with CH$_2$Cl$_2$:MeOH (95:5). Evaporation of the appropriate fractions gave the title compound as a white solid (0.15 g, 15%); m.p., 212°–214° C.; [α]$^{20}$ −144° (c 1, MeOH); δH (250 MHz, CDCl$_3$, 1 conf.), 0.75–1.10 (39H, m, CH$_3$ of Val, (Me)Val, (Me)Leu, Abu), 1.15–1.35 (6H, d×d, CH$_3$ of L-Ala, D-Ala), 1.55–1.50 (10H, br.m., β-CH$_2$ of Abu, (Me)Leu), 1.85–2.55 (6H, β-CH of (Me)Val, γ-CH of (Me)Leu), 2.79–3.50 (21H, series of s, N-CH$_3$), 3.85 (2H, d, β-CH$_2$(Me)Ser), 4.45–4.55 (1H, m, α-CH-Ala), 4.60–4.75 (5H, m, α-CH-Sar, (Me)Val, Val (Me)Ser —OH), 4.79–4.85 (1H, m, α-CH-D-Ala), 4.49–5.10 (1H, m, α-CH-Abu), 5.15–5.28 (2H, d×d, α-CH-(Me)Leu), 5.45–5.55 (1H, t, α-CH-(Me)Ser), 5.60–5.75 (2H, d×d, α-CH, (Me)Leu), 7.15 (1H, d, N-H-D-Ala), 7.35 (1H, d, NH-Val), 7.95 (1H, d, NH-Ala), and 8.40 (1H, d, NH-Abu); m/z 1120 (M+1, FAB); R$_t$ 11.4 min.

EXAMPLE 40

Cyclo[Hyp-Abu-Sar-(Me)Leu-Val-(Me)Leu-Ala-D-Ala-(Me)Leu-(Me)Leu-(Me)Val]

DMAP (0.42 g, 2.05 mM, 5 equiv.), followed by the Castro reagent BOP (1.23 g, 1.64 mM, 4 equiv.) were added to a rapidly stirring solution of H-Hyp-Abu-Sar-(Me)Leu-Val-(Me) Leu-Ala-D-Ala-(Me)Leu-(Me)Leu-(Me)Val-OH (0.80 g, 0.41 mM, 1 equiv.; prepared as described in Example 27) in CH$_2$Cl$_2$ (21) and the resulting mixture stirred at room temperature for four days. The solution was then concentrated to (100 cm$^3$) and chromatographed on silica gel eluting with EtOAc/MeOH (97:3). Evaporation of the appropriate fractions afforded the title compound as a white solid, (0.24 g, 30%); m.p., 116°–168° C.; [α]$^{20}$ −240° (c 1, MeOH); δH (250 MHz, CDCl$_3$, 1 conf.), 0.81–1.01 (39H, m, CH$_3$ of Abu, Val, (Me)Leu, (Me)Val), 1.27 (3H, d, CH$_3$-D-Ala), 1.36 (3H, d, CH$_3$-L-Ala), 1.39–1.80 (10H, m, β-CH$_2$ of Abu, (Me)Leu), 1.82–2.38 (7H, m, β-CH of Val and (Me)Val, β-CH$_2$ of Hyp, and γ-CH of (Me)Leu), 2.68–2.69 (3H, d, N-CH$_3$), 3.11–3.12 (1H, m, α-CH-Sar), 3.25–3.30 (15H, series of s, N-CH$_3$), 3.84–3.89 (2H, d×d, α-CH-Hyp), 2.84–3.89 (2H, d×d, δ-CH$_2$-Hyp), 4.04–4.20 (1H, m, γ-CH of Hyp), 4.30–4.41 (1H, t, α-CH-L-Ala), 4.44 (1H, br.s., —OH), 4.47–4.89 (5H, m, α-CH of Val, (Me)Val, Sar, Abu and D-Ala), 4.93–5.09 (2H, m, α-CH, (Me)Leu), 5.13–5.31 (2H, d×d, α-CH, (Me)Leu), 5.34–5.69 (1H, d×d, α-CH-Hyp), 7.14 (1H, d, N-H-D-Ala), 7.45 (1H, d, NH-Val), 7.77 (1H, d, NH-L-Ala), and 8.65 (1H, d, NH-Abu); m/z 1133 (M+1, FAB); R$_t$ 10.2 min.

EXAMPLE 41

Cyclo-[(Dab(Fmoc)-Abu-Sar-(Me)Leu-Val-(Me)Leu-Ala-D-Ala-(Me)Leu-(Me)Leu-(Me)Val]

DMAP (0.20 g, 1.65 mM, 5 equiv.), followed by the Castro reagent BOP (0.58 g, 1.32 mM, 4 equiv.) were added to a rapidly stirring solution of H-Dab(Fmoc)-Abu-Sar-(Me)Leu-Val-(Me)Leu-Ala-D-Ala-(Me)Leu-(Me)Leu-(Me)Val-OH (0.45 g, 0.33 mM, 1 equiv.; prepared as described in Example 28) in CH$_2$Cl$_2$ (21) and the mixture stirred at room temperature for three days. The solution was concentrated to (50 cm$^3$) and chromatographed initially on SEPHADEX LH20 eluting with DMF and then on silica gel eluting with EtOAc/MeOH 97:3%. Evaporation of the appropriate fractions afforded the title compound as a white solid (0.17 g, 37%); m.p., 156°–157° C.; [α]$^{20}$ −190.2° (c 0.9, MeOH). Calculated for C$_{71}$H$_{112}$N$_{12}$O$_{13}$.2H$_2$O: C, 61.92; H, 8.43; N, 12.21. Found: C, 62.25; H, 8.39; N, 12.30%; δH (250 MHz, CDCl$_3$, 1 conf.), 0.78–1.12 (39H, m, CH$_3$ of (Me)Leu, Val, (Me)Val, Abu), 1.33–1.37 (6H, d×d, CH$_3$ of D-Ala, L-Ala), 1.40–1.72 (16H, m, β-CH$_2$ of (Me)Leu, Abu, Dab and γ-CH of (Me)Leu), 2.06–2.39 (2H, m, β-CH of Val, (Me) Val), 2.77–3.44 (18H, series of s, N-CH$_3$), 4.21–4.49 (5H, m, —CH$_2$ of Dab, α-CH of Sar and L-Ala), 4.51–5.28 [5H, m, α-CH), 5.37–5.44 (2H, d×d, α-CH (Me)Leu), 5.64–5.68 2H, m, α-CH, (Me)-Leu), 6.27–6.37 (1H, m, Dab-NH). 6.56 (1H, d, Dab-NH). 7.31 (1H, d, NH-D-Ala). 7.34–7.77 (9H, m, ArH and NH-Val), 8.02 (1H, d, NH-L-Ala), and 8.62 (1H, d, NH-Abu); m/z 1341 (M+1, FAB); R$_t$ 13.4 min.

EXAMPLE 42

Cyclo-[Dab-Abu-Sar-(Me)Leu-Val-(Me)Leu-Ala-D-Ala-(Me)Leu-(Me)Leu-(Me)Val]

Cyclo-[Dab(Fmoc)-Abu-Sar(Me)Leu-Val-(Me)Leu-Ala-D-Ala(Me)Leu-(Me)Leu-(Me)Val](90 mg, 0.07 mM; prepared as described in Example 41) was stirred in piperidine (1 cm$^3$) at room temperature for thirty minutes and then poured into water (20 cm$^3$). The piperidine-dibenzofulvene adduct was filtered and the filtrate evaporated to dryness. The residue was applied on SEPHADEX LH20 eluting with DMF; evaporation of the appropriate fractions afforded the title compound as a white solid; m.p., 160°–164° C.; [α]$^{20}$ −181° (c 1.1, MeOH); m/z 1118 (M+1, FAB); R$_t$ 12.1 min.

EXAMPLE 43

Cyclo-[(Me)Ser-Nva-Sar-(Me)Leu-Val-(Me)Leu-Ala-D-Ala-(Me)Leu-(Me)Leu-(Me)Val]

H-(Me)Ser-Nva-Sar-(Me)Leu-(Me)Val-(Me)Leu-Ala-D-Ala-(Me)Leu-(Me) Leu-(Me)Val-OH (400 mg, 0.31 mM; prepared as described in Example 30) was dissolved in CH$_2$Cl$_2$-THF (1:1) (80 ml). To this was added DMAP (0.20 g, 2.17 mM, 7 equiv.), followed by the Castro reagent BOP (0.822 g, 1.86 mM, 6 equiv.) The solution was stirred at room temperature for three days and was concentrated by evaporation on a rotary evaporator to 20 ml, this solution was chromatographed on (i) a silica gel column eluting with CH$_2$Cl$_2$+5% MeOH, (ii) SEPHADEX LH20 eluting with DMF. Evaporation of the appropriate fraction afforded the title compound as white crystals (from ether/petroleum ether) (72 mg, 20% yield); m.p., 112°–114° C.; [α]$^{24}$ −136°, (c 1.0, MeOH); m/z 1135 (M+1, FAB); R$_t$ 11.6 min.

EXAMPLE 44

Cyclo-[(Me)Thr-Nle-Sar-(Me)Leu-Val-(Me)Leu-Ala-D-Ala-(Me)Leu-(Me)Leu-(Me)Val]

H-(Me)Thr-Nle-Sar-(Me)Leu-Val-(Me)Leu-Ala-D-Ala-(me)Leu-(Me)Leu-(Me)Val (300 mg, 0.26 mM) was dissolved at ambient temperature in dichloromethane (800 ml). To this was added DMAP (0.21 g, 1.82 mM, 7 equiv.), followed by the Castro reagent BOP (0.650 g, 1.77 mM. 6 equiv.). The solution was stirred at room temperature for three days and solvent evaporated. The oily residue was subjected to chromatography on SEPHADEX LH20 eluting with DMF. Evaporation of the appropriate fractions afforded the title compound (29) as white crystals (from ether/petroleum ether) (46 mg, 14% yield); m.p., 94°–95° C.; [α]$^{24}$ −168° (c, 1.0, CHCl$_3$); m/z 1162 (M+, FAB); R$_t$ 11.2 min.

EXAMPLE 45

Cyclo-[(Me)Ser-Nle-Sar-(Me)Leu-Val-(Me)Leu-Ala-D-Ala-(Me)Leu-(Me)Leu-(Me)Val]

H-(Me)Ser-Nle-Sar-(Me)Leu-Val-(Me)Leu-Ala-D-Ala-(Me)Leu-(Me)Leu-(Me)Val-OH (450 mg, 0.39 mM; prepared as described in Example 34) was dissolved in THF-$CH_2Cl_2$ (1:1) (900 ml) at room temperature. To this was added DMAP (0.33 g, 2.7 mM, 7 equiv.), followed by the Castro reagent BOP (0.975 g, 2.2 mM, 6 equiv.). The solution was stirred at room temperature for three days and then the solvent was evaporated and the oily residue chromatographed twice; firstly on a silica gel column eluting with $CH_2Cl_2$ plus 5% MeOH and then on LH20 gel filtration column eluting with DMF. Evaporation of the appropriate fraction afforded the title compound as white crystals (from ether/petroleum ether) (67 mg, 16%; m.p., 108°–110° C.; $[\alpha]^{23} -141°$ (c, 1.0, MeOH); m/z 1149 (M+1, FAB); $R_t$ 11.4 min.

EXAMPLE 46

Cyclo[(Hyp-Nle-Sar-(Me)Leu-Val-(Me)Leu-Ala-D-Ala-(Me)Leu-(Me)Leu-(Me)Val]

DMAP. (0.84 g, 4.1 mM, 7 equiv.), followed by the Castro reagent BOP (2.61 g, 3.48 mM, 6 equiv.) were added to a rapidly stirred solution of H-Hyp-Nle-Sar-(Me)Leu-Val-(Me)Leu-Ala-D-Ala-(Me)Leu-(Me)Leu-(Me)Val-OH (1.18 g, 1 mM, 1 equiv.; prepared as described in Example 36) in $CH_2Cl_2$ (2.5 l), and the resulting stirred at room temperature for three days. The solution was concentrated to (100 cm$^3$) and chromatographed on silica gel eluting with EtOAc/MeOH (97:3). Evaporation of the appropriate fractions gave a white crystalline solid (0.30 g, 26%); m.p., 145° C.; $[\alpha]^{23} -152.4°$ (c 1.0, $CH_3OH$); δH (250 MHz, CDCl$_3$), 0.70–1.26 [36H, m, $CH_3$ of (Me)Leu, Val, (Me)Val, Nle], 1.26–1.28 (3H, d, $CH_3$-D-Ala), 1.35–1.38 (3H, d, $CH_3$-Ala), 1.43–1.84 (12H, m. β,γ,δ-$CH_2$-Nle), 1.85–2.44 (8H, m, β-CH-Val, (Me)Val, β-$CH_2$-Hyp, γ-CH, (Me)Leu), 2.68–3.30 (18H, series of s, N-$CH_3$), 3.84–3.90 (2H, d×d, δ-CH, Hyp), 4.29–4.33 (1H, m, γ-CH, Hyp), 4.41–4.68 (1H, α-CH, L-Ala), 4.70 (1H, br.s., —OH). 4.72–4.95 (4H, m, α-CH-D-Ala, Val, (Me)Val, Sar), 4.96–5.16 (2H, m, α-CH, Hyp, Nle). 5.30–5.36 (2H, d×d, α-CH, (Me)Leu), 5.64–5.74 (2H, d×d, —CH, (Me)Leu), 7.23 (1H, d, NH-D-Ala), 7.77 (1H, d, NH-Val), 8.10 (1H, d, NH-L-Ala), and 8.68 (1H, d, NH-Nle); m/z 1160 (M+1, FAB); $R_t$ 10.8 min.

EXAMPLE 47

In vitro tests of activity

The activity of compounds of formula (I) was compared with that of cyclosporin A (CsA) in a mixed leucocyte culture using mouse lymphocytes and allogeneic dendritic cells (DC). In this procedure antigens on the DC surface are presented to the lymphocytes which are stimulated to proliferate thus mimicking a graft rejection response in vitro. Cyclosporin blocks this reaction by an effect on the function of the antigen-presenting DC as described by Knight and Bedford, Transplantation Proceedings, 1987, 19, 320. The cyclosporin-like activity of the compounds of the present invention can therefore be studied by comparing the response of lymphocytes to DC, in the presence of the compound or of CsA, in terms of $^3H$ thymidine uptake for incorporation into DNA.

Preparation of lymphocytes

Mouse lymph nodes were pressed through wire mesh to give a single cell suspension. The suspension was incubated on a nylon wool column for 2 hours, and non-adherent cells eluted to give a T-lymphocyte enriched cell suspension.

Preparation of DC

Single cell suspensions of mouse spleens were incubated overnight at 37° C. in plastic culture flasks. Non-adherent cells were spun over a 14.25% w/v metrizamide gradient and the low-density DC recovered.

Test procedure

DC were pulsed for 2 hours with a range of doses of the compound under test or of CsA, then washed 4 times. Mixed leukocyte cultures were set up in Terasaki plates in 20 μl hanging drops containing 500 DC and 100,000 lymphocytes. Uptake of $^3H$ thymidine (2 Ci/mM) into DNA in a 2 hour pulse on day 3 of culture was measured. The procedure is described in detail by Knight in "Lymphocytes—a practical approach", Edited by Klaus, IRL Press (Oxford/Washington), 1987, 189.

Typical results are illustrated in the accompanying Figure for the compounds

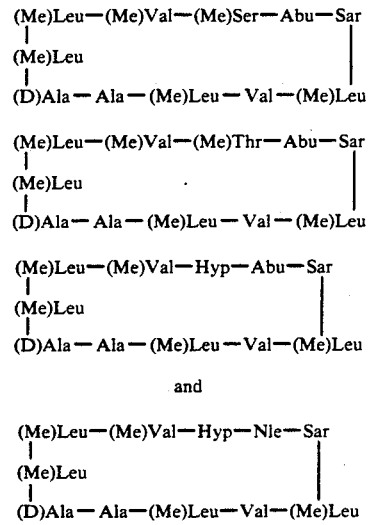

and (Me)Leu—(Me)Val—Hyp—Nle—Sar
|  |  |
(Me)Leu  |
|  |
(D)Ala—Ala—(Me)Leu—Val—(Me)Leu the first of which is identified in the Figure as (A1) and (A2). the two forms differing in stereochemistry, the second as (B) and the third and fourth as (C) and (D) respectively, each of these having a 4-hydroxyproline residue which is of the trans configuration.

I claim:

1. A cyclosporin having the structure

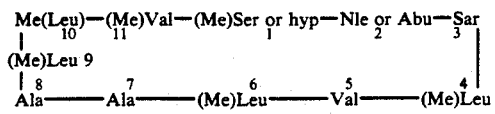

wherein all amino acid residues are in the L-configuration at the alpha carbon atoms except for the Ala residue in position 8 which is in the D-configuration at the alpha carbon atoms.

* * * * *